(12) United States Patent
Takahashi

(10) Patent No.: US 9,169,487 B2
(45) Date of Patent: Oct. 27, 2015

(54) **METHOD FOR PRODUCING A LARGE REGION DUPLICATION OF *ASPERGILLUS* CHROMOSOME**

(75) Inventor: Tadashi Takahashi, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 0 days.

(21) Appl. No.: 13/704,029

(22) PCT Filed: May 25, 2011

(86) PCT No.: PCT/JP2011/062009
§ 371 (c)(1),
(2), (4) Date: Jan. 29, 2013

(87) PCT Pub. No.: WO2011/158623
PCT Pub. Date: Dec. 22, 2011

(65) Prior Publication Data
US 2013/0171319 A1    Jul. 4, 2013

(30) Foreign Application Priority Data

Jun. 17, 2010    (JP) ................. 2010-138637

(51) Int. Cl.
*C12N 15/80* (2006.01)
*A23L 1/238* (2006.01)

(52) U.S. Cl.
CPC ............... *C12N 15/80* (2013.01); *A23L 1/238* (2013.01)

(58) Field of Classification Search
None
See application file for complete search history.

(56) References Cited

U.S. PATENT DOCUMENTS 6,352,841 B1 * 3/2002 Lehmbeck .................. 435/69.1

FOREIGN PATENT DOCUMENTS

| EP | 2 420 561 | 2/2012 |
|---|---|---|
| JP | 2009-95279 | 5/2009 |
| JP | 4469014 | 3/2010 |
| WO | 98/45455 | 10/1998 |
| WO | WO 9845455 A1 * | 10/1998 |

OTHER PUBLICATIONS d'Enfert, Current Genetics, 1996, vol. 30 oages 76-82.*
Machida et al., Nature, 2005, vol. 438, pp. 1157-1161.*
Gouka et al., Nature Biotechnology, 1999, vol. 17, pp. 598-601.*
International Search Report issued Aug. 2, 2011 in International (PCT) Application No. PCT/JP2011/062009.
J. Argueso et al., "Double-strand breaks associated with repetitive DNA can reshape the genome", PNAS, vol. 105, No. 33, pp. 11845-11850, Aug. 19, 2008.
J. Halbrook et al., "Mutations in the *Saccharomyces cerevisiae CDC1* Gene Affect Double-Strand-Break-Induced Intrachromosomal Recombination", Molecular and Cellular Biology, vol. 14, No. 12, pp. 8037-8050, Dec. 1994.
European Search Report issued Mar. 20, 2013 in corresponding European Application No. 11795531.0.
Takahashi, Tadashi, et al., "Generation of Large Chromosomal Deletions in Koji Molds *Aspergillus oryzae* and *Aspergillus sojae* via a Loop-Out Recombination", Applied and Environmental Microbiology, vol. 74, No. 24, pp. 7684-7693, 2008.

* cited by examiner

*Primary Examiner* — Anne Gussow
*Assistant Examiner* — Mindy G Brown
(74) *Attorney, Agent, or Firm* — Wenderoth, Lind & Ponack, L.L.P.

(57) ABSTRACT

Disclosed is a technique which is for duplicating across a wide region any large region on a chromosome of a fungus belonging to *Aspergillus* strain, and which enables the stable and systematic acquisition of a previously un-acquirable fungus belonging to the *Aspergillus* strain having novel traits. Disclosed is a transformant wherein a transformation marker gene sequence is arranged on the outside of terminals (5', 3') of a region so as to sandwich an arbitrary region of a chromosome, and chromosome duplication has taken place by means of homologous recombination after double strand breakage generated in a homologous region inside the gene. Also disclosed is a method for duplicating an arbitrary region of a chromosome of a fungus belonging to *Aspergillus* strain by culturing said transformant.

8 Claims, 13 Drawing Sheets

METHOD FOR PRODUCING A LARGE REGION DUPLICATION OF *ASPERGILLUS* CHROMOSOME

TECHNICAL FIELD

The present invention relates to a technique for duplicating any large region on a chromosome of a fungus belonging to *Aspergillus*.

BACKGROUND ART

*Aspergillus* strains such as *Aspergillus sojae* and *Aspergillus oryzae* have been industrially used in the production of brewed food such as soy sauce, sake (rice wine), soybean paste, etc. With a recent determination of the whole genomic sequence of *Aspergillus oryzae* and development of an exhaustive analysis of gene expression using a micro-array, it has been expected that genetic modification of their genes, especially their chromosomal modification would increase the productivity of an enzyme and improve a growth rate of these filamentous fungi.

Furthermore, enzymes produced by the *Aspergillus* strains are utilized in a variety of industries. For example, in the production of soy sauce, the traditional food in Japan, various enzymes produced by the *Aspergillus* strains are used. The *Aspergillus* strains are cultured with starting materials such as soybean and wheat so as to produce the various enzymes, which will degrade proteins, carbohydrates, lipids, etc. of the soybean and wheat and promote lactic acid fermentation and yeast fermentation in the following steps. If a large amount of the above degradative enzymes is produced, the productivity can be much improved due to the increase in a utility factor of the starting materials and a rate of squeezing. In addition to that, since substrates shall be sufficiently provided to the lactic acid fermentation and yeast fermentation so as to properly carry out the fermentation processes, the quality of soy sauce can be improved to a large extent.

Unlike *Aspergillus nidulans*, *niger*, *fumigatus* and *awamori* that have a mononuclear generation, koji molds such as *Aspergillus sojae* and *Aspergillus oryzae* are always kept in a multinuclear state in their whole life cycle including in a conidium condition, and their sexual generation has not yet been observed. Their nuclear-distribution mechanism from a parent cell to a daughter cell has not yet been revealed, either. Accordingly, a mutant cannot be produced by means of mating between strains or RIP (Repeat Induced Mutation), which makes it difficult to study their genetics. As a result, the genetic analysis of *Aspergillus sojae* and *Aspergillus oryzae* has fallen behind in spite of their industrially very high utility.

As it is therefore very important from an industrial point of view to breed *Aspergillus* strains of high utility such as those having high productivity of various enzymes, methods for breeding have been vigorously developed for the above purpose. There are two prominent types of such breeding methods, i.e., mutation and genetic recombination (genetic modification) methods.

The mutation method uses various mutation treatments such as X-ray, ultraviolet ray, and heavy ion beam. Useful characteristics have been used as an index for screening strains having various enzyme activities and excellent fermentation properties. Recently, the strains having such useful characteristics have been analyzed by means of genomic information to reveal that the duplication of chromosome is important for providing the *Aspergillus* strains with such useful characteristics. An *Aspergillus* strain having duplication of such a large scale as 900 kb or more was obtained by means of mutation treatment method (Patent Literature 1). It was already reported that repeated sequences were found with a high frequency at a boundary region of the duplicated region on the chromosome by analysis of a yeast obtained by means of γ-ray radiation (Non Patent Literature 1).

However, the mechanism of such duplication of the chromosome has not yet been revealed. Accordingly, it has been just possible to accidentally obtain a strain having duplication of a region relating to an enzyme by means of conventional mutation treatments and screening based on activity of said enzyme. However, since mutation will actually occur on various sites at random on the chromosome, it has been impossible to duplicate a particular region on the chromosome of the *Aspergillus* strains. Furthermore, it is well known that back mutation or revertant (elimination of the duplicated chromosome) will occur with a high frequency due to recombination between the homologous sequences in said strain having the duplication obtained by means of the conventional mutation treatments.

On the other hand, the genetic recombination method utilizes transformation to introduce a target gene into the *Aspergillus* strains for breeding. Conventionally, the gene that can be introduced in said method has 5~6 kb. However, in order to actually obtain such useful *Aspergillus* strains as those having a high enzyme-productivity, it would be necessary to include a promoter region, a terminator region and a marker gene for screening, if necessary, in addition to the target gene region in a region to be introduced, which could enlarge the size of said region up to 10 kb or more.

As seen form the above description, there has exited no technique that enables the duplication of a relatively large region at an arbitrary site on the chromosome.

CITATION LIST

Patent Literature

[PTL 1] Japanese Patent No. 4469014

Non Patent Literature

[NPL 1] Argueso et al., (2008) Proc. Natl. Acad. Sci., USA 105:11845-11850

SUMMARY OF INVENTION

Technical Problem

Purpose of the present invention is therefore to provide a technique to duplicate across a wide region any large region on a chromosome of a fungus belonging to *Aspergillus*, so that it will enable for us to stably and systematically acquire an *Aspergillus* strain having a novel trait, which was unacquirable by conventional techniques.

Solution to Problem

The present inventor has found that a strain having a large-region duplicate on its chromosome can be prepared by constructing a transformant wherein the sequences of a transformation marker gene such as pyrG gene are located at 5' and 3' end (terminal) of any region on the chromosome so that said region is sandwiched by these sequences, followed by duplication of said region by means of a homologous recombination via a repairing mechanism after a double-strand break (scission) that occurs in homologous regions in the transformation marker genes, and selection of such transformant based on the transformation marker, which has led to the completion of the present invention.

The present invention is therefore related to the following aspects.

[Aspect 1]
A transformant which is characterized by being constructed by integrating a transformation marker gene with deficiency in a terminal part at one of the 5' or 3' end of its coding region into the outside of one of the 5' or 3' end of a targeted region to be duplicated on a chromosome of a fungus belonging to *Aspergillus*, and the transformation marker gene with deficiency in a terminal part at the other end of its coding region into the outside of the other end of the targeted region, so that the targeted region is sandwiched between the transformation marker genes with the deficiency in the terminal part at the 5' and 3' ends, respectively, wherein a sequence adjacent to the deficiency of each integrated transformation marker gene is located at an opposite side of the targeted region.

[Aspect 2]
The transformant according to Aspect 1, wherein a middle portion that is present in common in the coding region of the transformation marker genes with the deficiency in the terminal part at either the 5' or 3' end of its coding region has about 100 bp~about 2 kb sequence.

[Aspect 3]
The transformant according to Aspect 1 or 2, wherein the transformation marker gene is selected form the group consisting of pyrG, sC and niaD.

[Aspect 4]
The transformant according to any one of Aspects 1 to 3, wherein a restriction enzyme recognition site has been introduced in advance into a homologous sequence region that is present in both or either of the middle portion of the coding region of the transformation marker genes.

[Aspect 5]
The transformant according to Aspect 4, wherein the restriction enzyme is selected from the group consisting of I-sceI, I-ceuI, PI-pspI and PI-sceI.

[Aspect 6]
The transformant according to Aspect 4 or 5, wherein the restriction enzyme recognition site has been introduced by a homologous recombination.

[Aspect 7]
The transformant according to any one of Aspects 1 to 6, wherein the fungus belonging to *Aspergillus* is *Aspergillus sojae* or *Aspergillus oryzae*.

[Aspect 8]
A method for duplicating an arbitrary region on the chromosome of a fungus belonging to *Aspergillus*, comprising:
(1) culturing the transformant according to any one of Aspects 1 to 7;
(2) obtaining a fungus strain wherein the targeted region has been duplicated by means of a homologous recombination between corresponding chromosomes via a repairing mechanism after a double-strand break (breakage) in homologous sequence regions that are present in common in the middle portion of the coding region of the transformation marker genes integrated into outside of the 5' and 3' ends of the targeted region, respectively; and
(3) selecting the fungus strain wherein the targeted region has been duplicated by means of a trait based on the transformation marker gene with a full length of the coding region that has been constructed due to the homologous recombination.

[Aspect 9]
The method according to Aspect 8, wherein the transformant is in a multinuclear state.

[Aspect 10]
The method according to Aspect 8 or 9, wherein the transformant is maintained in a protoplast state, and then cultured.

[Aspect 11]
The method according to any one of Aspects 8 to 10, wherein the homologous recombination is induced by culturing the transformant under the action of a restriction enzyme.

[Aspect 12]
The method according to Aspect 11, wherein the transformant in the protoplast state is mixed with the restriction enzyme in the presence of a fusion auxiliary agent so as to make the restriction enzyme affect the transformant.

[Aspect 13]
A fungus belonging to *Aspergillus* having a duplicated region on its chromosome, to which is obtained by the method according to any one of Aspects 8 to 12.

[Aspect 14]
The fungus according to Aspect 13, wherein the fungus belonging to *Aspergillus* is *Aspergillus sojae* or *Aspergillus oryzae*.

[Aspect 15]
The fungus according to Aspect 13 or 14, wherein the duplicated region has several tens to several hundreds kb.

[Aspect 16]
Soy sauce produced by using the fungus belonging to *Aspergillus* according to any one of Aspects 13 to 15.

Advantageous Effects of Invention

The present invention has enabled the duplication of any large region of several tens to several hundreds kb (for example, about 200 kb~about 500 kb) on the chromosome of *Aspergillus* strains. No such technique existed. Furthermore, since the method according to the present invention uses only endogenous genes of a host and any exogenous gene will not remain in the resulting strain having the duplication (self-cloning stain), it is a very remarkable breeding method of microorganisms used for the production of foods such as fermentation of soy sauce, for example, *Aspergillus* strains for soy sauce.

Furthermore, in the *Aspergillus* strains having the duplicated region on its chromosome and obtained by the present method, if the duplicated chromosome is eliminated due to recombination between the homologous sequences aligning in tandem, the transformation marker gene such as pyrG will be simultaneously eliminated so as to make the strain become auxotrophy such as uridine requirement. As a result, the elimination of the duplicated chromosome can be prevented due to selective pressure since such strain is no longer able to grow in an usual medium. Thus, the method according to the present invention is an excellent method for producing a strain having the duplicated chromosome without the fear of back mutation.

DESCRIPTION OF EMBODIMENTS

Figure 1:
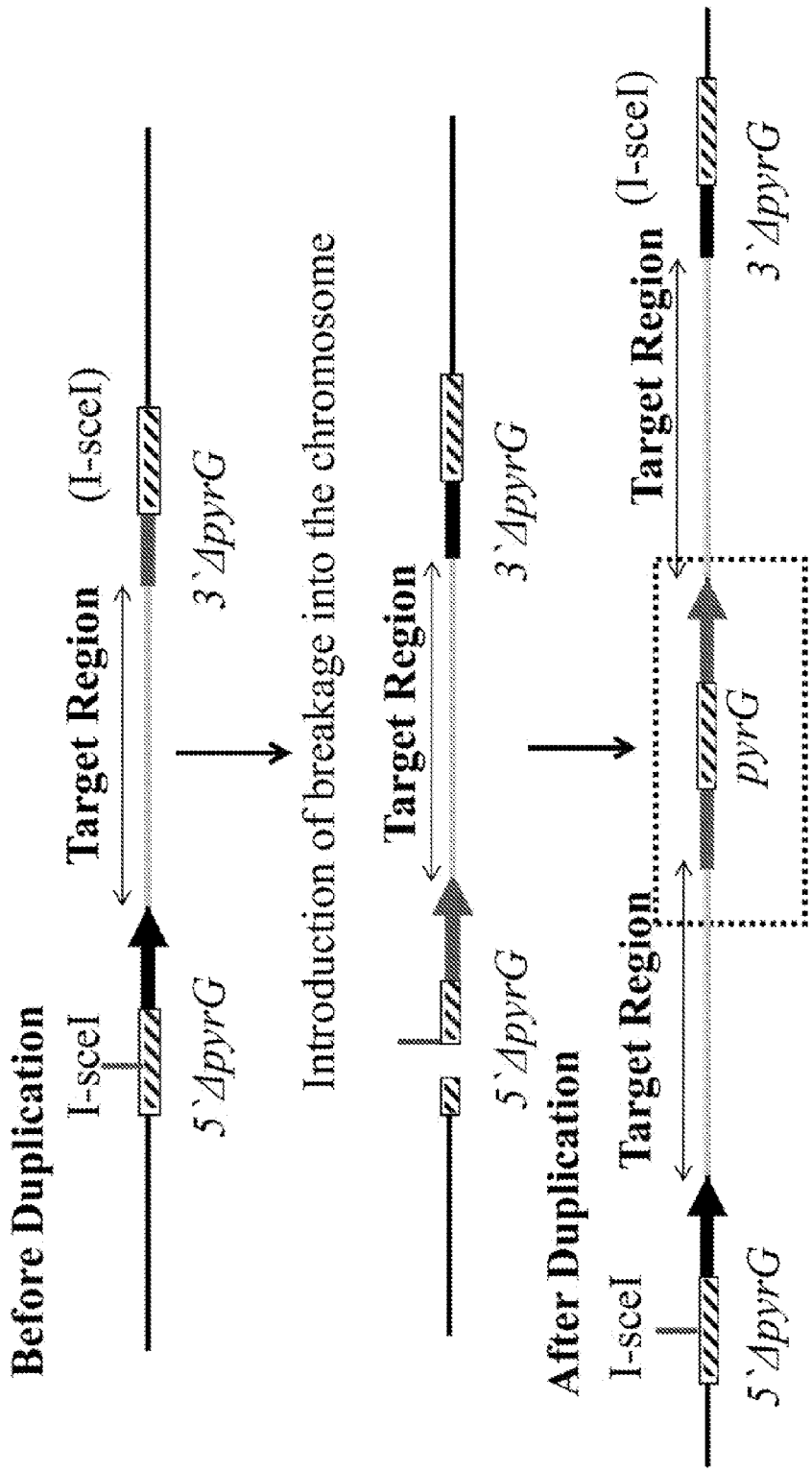
FIG. 1 is a schematic figure showing the method of the present invention.

The fungus belonging to *Aspergillus* that is used as a parent strain according to the present invention includes any strains such as that of *Aspergillus sojae, Aspergillus oryzae, Aspergillus niger, Aspergillus awamori* and the like, strains of *Aspergillus sojae* and *Aspergillus oryzae* being preferable.

Their specific strains include, for example, those deposited at a public depository institution and easily available to those skilled in the art such as *Aspergillus sojae* 262 (FERM P-2188), *Aspergillus sojae* 2165 (FERM P-7280), *Aspergillus sojae* (ATCC 42251), *Aspergillus oryzae* (IAM2638) and *Aspergillus oryzae* RIB40 (NBRC100959).

It is known that a foreign DNA will be integrated into chromosome via repairing mechanism at the time of double-strand break (DSB) of chromosomal DNA. There are two kinds of mechanisms in the repairing, that is, homologous recombination and non-homologous recombination (non-homologous end joining). The integration will occur through a region having homology with the foreign DNA in the case of the homologous recombination. On the other hand, the integration will do at a random site of the chromosome regardless of a to sequence of the foreign DNA in the case of the non-homologous recombination. It is conceived that the two recombination mechanisms will function in equilibration (Ristic et al., Nucl. Acids Res. (2003) 31:5229-5237).

A series of genes belonging to a so-called "rad52 group" take an essential role in the homologous recombination, which includes rad50, 51, 52, 54, Mre11 and XRS2 (Kooistra et al. 2004). The homologous recombination mechanism has been confirmed to exist in a wide range of organisms from bacteria to eukaryotic organisms. A uvsC gene has been cloned and studied using *Aspergillus nidulans*, an experimental strain belonging to *Aspergillus*, having a mononuclear conidium (van Heemst et al., Mol. Gen. Genet (1997) 254: 654-64), and it was reported that the frequency of the homologous recombination would be improved by increasing expression frequency of the above genes up to a certain level (Natsume et al. Biosci. Biotechnol. Biochem. (2004) 68:1649-1656).

On the other hand, it has been revealed that the non-homologous recombination will proceed with non-homologous end joining mechanism that is completely different form the homologous recombination mechanism. Genes such as ku70, ku80, Xrcc4, LIG4 and DNAPKcs are known to take an essential role in this recombination mechanism. It is known that Ku70 and Ku80 will act as a hetero dimmer, form a complex with a nucleotide kinase (XRCC4) and DNA Ligase IV, and promote the non-homologous end joining by joining with a DNA end at the time of cleavage of the DNA double-strand break for its repairing (Walker et al., Nature (2001) 412:607-614). The non-homologous recombination via ku gene has been recognized only in eukaryotic organisms.

By using the transformant according to the present invention, it has been now possible to duplicate any large region of several tens to several hundreds kb on the chromosome of an *Aspergillus* strain. Thus, the transformant according to the present invention is characterized by being constructed by integrating a transformation marker gene with deficiency in a terminal part at one of the 5' or 3' end (either the 5' end or 3' end) of its coding region into the outside of one of the 5' or 3' end (either the 5' end or 3' end) of a targeted region to be duplicated on a chromosome of the fungus belonging to *Aspergillus*, and a transformation marker gene with deficiency in a terminal part at the other end of its coding region into the outside of the other end of the targeted region, so that the targeted region is sandwiched between the two transformation marker genes with the deficiency in the terminal part at the 5' and 3' ends, respectively, wherein a sequence adjacent to the deficiency of each integrated transformation marker gene (a sequence at a terminal region having the deficiency) is located at an opposite side of the targeted region.

Specifically, a transformation marker gene with deficiency in a terminal part at the 5' end of its coding region (5' terminal region of a base sequence with an appropriate length) is integrated into the outside of the 5' end of a targeted region to be duplicated on a chromosome of a fungus belonging to *Aspergillus*, and a transformation marker gene with deficiency in a terminal part at the 3' end of its coding region (3' terminal region of a base sequence with an appropriate length) is integrated into the outside of the 3' end of said targeted region. Alternatively, the transformation marker gene with deficiency in the terminal part at the 3' end of its coding region may be integrated into the outside of the 5' end of said targeted region, and the transformation marker gene with deficiency in the terminal part at the 5' end of its coding region may be integrated into the outside of the 3' end of said targeted region.

In each of the above cases, it is necessary that the sequences adjacent to the deficiency at the 5' and 3' end of the two integrated transformation marker genes that sandwich the targeted region to be duplicated are located at the opposite side of the targeted region, respectively During the culture of the transformant having the above structure, the homologous recombination between the corresponding chromosomes via a repairing mechanism after or at the double-strand break of the homologous sequence regions (a part presented with hatched lines in FIGS. 1, 2 and 10) that are present in common in the middle portion of the coding region of the transformation marker genes integrated into outside of the 5' and 3' ends of the targeted region, respectively, resulting in the strains wherein the targeted region has been duplicated. The "corresponding chromosomes" used herein means corresponding chromosomes contained in a multinuclear of the transformant such as multiple $2^{nd}$ and $8^{th}$ chromosomes that comprise many genes encoding useful substances, for example, various enzymes.

A transformant wherein a gene involved in the non-homologous recombination is deleted or suppressed (Japanese Patent Publication 2006-158269) may be used as the *Aspergillus* strain in the present invention.

It is preferred that the transformation marker gene integrated into the outside of the 5' and 3' ends of the targeted region to be duplicated has deficiency in its terminal part at either the 5' or 3' end of its coding region, so that it will leave a base sequence long enough to efficiently generate homologous recombination, for example, a base sequence with several hundreds bp or more, several hundreds bp to several kb (e.g., about 100 bp to about 2 kb) in the middle portion of the coding region of the transformation marker gene. In other words, it is preferred that the base sequence with said length is kept in the middle portion of the coding region of the original transformation marker gene in both of the transformation marker genes integrated into the outside of the 5' and 3' ends of the targeted region to be duplicated. Accordingly, the length of base sequence to be deleted in its terminal part at the 5' or 3' end of the coding region of the original transformation marker gene may be optionally determined by those skilled in the art depending on a kind, full length and the like of the transformation marker gene to be used. For example, said length may be usually about 0.4 kb~about 1.4 kb in the case of pyrG gene. Additionally, it is not necessary for both of the defective base sequences in the terminal part at the 5' and 3' ends to have the same length to each other.

During the culture of the transformant according to the present invention, the full length of the coding region of the transformation marker gene has been constructed due to the homologous recombination in a fungus strain simultaneously as the targeted region has been duplicated. As a result, such strain can be selected or distinguished by means of the trait based on the transformation marker gene from a fungus strain wherein the targeted region is not duplicated, i.e., the full length of the coding region of the transformation marker gene is not constructed.

Although there is no limitation in the transformation marker gene to be used in the present invention, pyrG sC and niaD may be exemplified as a positive selection marker gene, which will enable the selection of the fungus strain wherein the targeted region has been duplicated by means of a trait that can compensate various kinds of auxotrophy such as uridine requirement, sulfur assimilation and nitric assimilation.

These marker genes may be also used for a negative selection wherein a strain is cultured in a culture medium comprising a drug for selection so that a cytotoxic substance that has been converted from the drug by an expressed product of said genes will kill the strain.

Furthermore, a restriction enzyme recognition site for an appropriate restriction enzyme known in the art such as I-sceI. I-ceuI, PI-pspI and PI-sceI may be introduced in advance into both or either of the homologous sequence regions that are present in the middle portion of the coding region of the transformation marker genes integrated into the outside of the 5' and 3' ends of the targeted region to be duplicated, respectively. The above restriction enzyme recognition site may be introduced by any means known for those skilled in the art such as homologous recombination method.

Figure 2:
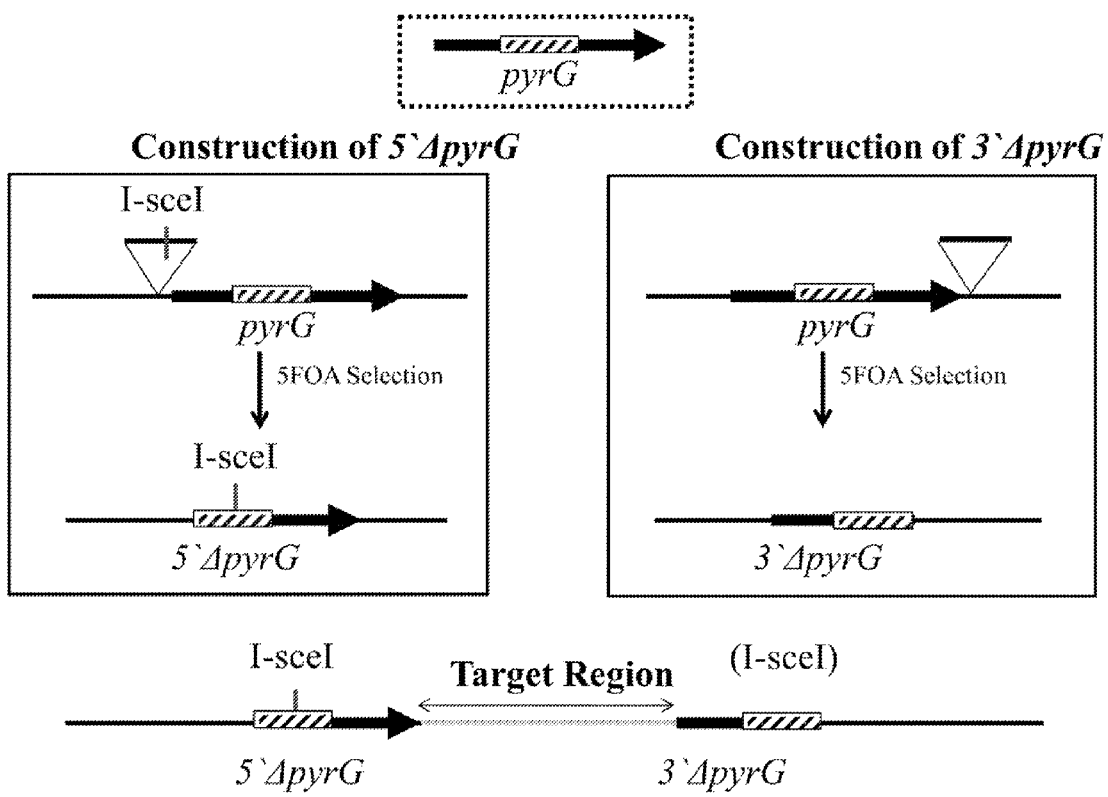
FIG. 2 shows a preparation of 5' ΔpyrG or 3' ΔpyrG unit.

The present invention is therefore related to a method for duplicating an arbitrary region on the chromosome of a fungus belonging to *Aspergillus*, whose schematic figure is shown in FIG. 1. Thus, the method comprises:
(1) culturing the transformant according to the present invention;
(2) obtaining a fungus strain wherein the targeted region has been duplicated by means of a homologous recombination between corresponding chromosomes via a repairing mechanism after (or "at") a double-strand break in homologous sequence regions that are present in common in the middle portion of the coding region of the transformation marker genes integrated into outside of the 5' and 3' ends of the targeted region, respectively; and
(3) selecting the fungus strain wherein the targeted region has been duplicated by means of a trait based on the transformation marker gene wherein a full length of its coding region has been constructed due to the homologous recombination.

The above method utilizes the homologous recombination via the repairing mechanism that will function when the double-strand break in the homologous sequence regions that are present in common in the middle portion of the coding region of the transformation marker genes occurs with an appropriate frequency. In the method according to the present invention, it is possible to increase the efficiency of said homologous recombination by bringing the transforman into a protoplast state with any method known for those skilled in the art, keeping it for a certain amount of time (for example, several-tens minutes~an hour) under appropriate conditions, and then culturing it. As *Aspergillus sojae* and *Aspergillus oryzae* are always kept in a multinuclear state in their whole life cycle including a conidium condition, it is considered that the homologous recombination may be easily generated between the corresponding chromosomes. On the other hand, although the other *Aspergillus* strains such as *Aspergillus nidulans, niger, fumigatus* and *awamori* have a mononuclear generation, the protoplast in the multinuclear state can be easily prepared from their mold hypha.

Furthermore, the homologous recombination may be induced by culturing the transformant under the action of an appropriate restriction enzyme known in the art such as I-sceI, I-ceuI, PI-pspI and PI-sceI in the case where a recognition site for the restriction enzyme has been introduced in advance into the transformation marker genes. Specifically, the transformant in the protoplast state may be mixed with the restriction enzyme in the presence of a fusion auxiliary agent such as PEG so as to make the restriction enzyme efficiently affect the transformant (protoplast PEG method).

The transformant according to the present invention may be constructed by any method known for those skilled in the art such as those described in the present specification. It may be cultured under appropriate conditions known in the art.

The present invention also relates to a fungus belonging to *Aspergillus* having the duplicated region with several tens to several hundreds kb (for example, about 200 kb~about 500 kb) on its chromosome, which is obtained by the method according to method according to the present invention. Since the targeted region subject to the duplication may be optionally selected, it is possible to obtain *Aspergillus* strains that are useful in the production of foods such as fermentation of soy sauce (for example, *Aspergillus* strains for soy sauce). The present invention is therefore related to foods such as soy sauce produced by using said fungus belonging to *Aspergillus*.

The present invention will be specifically explained below with reference to the examples, which should not be construed to limit the scope of the present invention.

EXAMPLE 1

Methods

Strains:
*Aspergillus oryzae* RP-1 strain (d pyrG) was used, which was a pyrG deletion strain (Takahashi et al. (2006) Biosci. Biotechnol. Biochem. 70:135-143) prepared from RIB40 strain (ATCC42149).
Culture Medium:
Polypepton dextrin (PD) medium (polypepton 1%, dextrin 2%, $KH_2PO_4$ 0.5%, $NaNO_3$ 0.1%, $MgSO_4$ 0.05%, casamino acid 0.1%, pH 6.0), CzapekDox (CZ) minimum medium, and 1.2M sorbitol CZ (as regeneration medium) were used. CZ medium containing 1.5 mg/ml 5 fluoroortic acid (5FOA: Sigma Co.) and 20 mM Uridine was used as a medium for positive selection of a pyrG (Uridine-auxotrophy) strain.

Transformation:

Conidium was inoculated on liquid PD medium (50 ml) containing 20 mM Uridine in a conical flask (150 ml) and subjected to shake culture for about 20 hours at 30° C., followed by collection of mycelium. The collected mycelium was washed with 0.7M KCl buffer, shaken gently in 0.7M KCl buffer containing 1% Lysing enzyme (Sigma Co.) for 3 hours at 30° C. to prepare protoplast. The resulting protoplast was washed with 1.2M sorbitol buffer, and transformed by means of a protoplast PEG method. Regeneration of the resulting transformant was carried out on 1.2M sorbitol CZ medium containing 0.5% agar.

Southern Hybridization:

Southern hybridization was carried out by a conventional manner using a Hybond-N+ membrane filter (Amersham Pharmacia). The detection was carried out with DIG Luminescent Detection Kit (Roche) in accordance with a method recommended by the manufacturer. H160, TD-A and TD-B probers were prepared with the primers of H160-iU and H160-iL, TD-AU and TD-AL, and TD-BU and TD-BL (Table 1), respectively, by means of DIG Probe Synthesis Kit (Roche), Construction of a Transformant with Duplication of Chromosome Using I-secI Strains having duplicated chromosomes were prepared as follows. PEG solution (20 μl) and I-secI (50 U or 0 U) were added to protoplast solution of bout 2×10$^7$/100 μl, which was then kept on ice for 40 min., mixed again with PEG solution (70 μl) and kept at a room temperature for 20 min., followed by regeneration on 1.2M sorbitol CZ medium plate. The strains that could grow were used as a candidate for the strains having duplicated chromosomes in the following analysis.

Comparison of the Number of Gene Copies in the Chromosome by Means of Quantitative PCR (Real-Time PCR)

The quantitative PCR was carried out using Mx3000P (Stratagene). The numbers of copies of H19, H74, H99 and H158 genes were compared between a parent strain F5 and the strains having duplicated chromosome by means of a relatively quantitative method with Rad52 as a mormalizer. The PCR was first kept for ten min. at 95° C., followed by repeating 45 times a cycle of heating for 20 seconds at 95° C., for 30 seconds at 58° C. and for 30 seconds at 72° C. The genes of Rad52, H19, H74, H99 and H158 were amplified using the primers of r52U-r52L, H19U-H19L, H74U-H74L, H99U-H99L and H158U-H158L, respectively (Table 1).

TABLE 1

Sequence of Primers used in the present invention

| Primer | Sequence (5'-3') | |
|---|---|---|
| H72U | TTCGAGATATTTTCGGTATCCAGCAAGACAS | EQ ID NO: 1 |
| H72L | TAGGTACTCTGATACCCAAACGGTCGAA | SEQ ID NO: 2 |
| H160U | TGTAGATGCAAATGATTAATATTCGTTCCCS | EQ ID NO: 5 |
| H160L | ACGTGATTAGAAAGTACAGCATCGTT | SEQ ID NO: 6 |
| H160-iU | CGACAGACTCTACCGGGTCGATGCC | SEQ ID NO: 7 |
| H160-iL | CCCCGGATCCAAGACTGTTGCGAGTT | SEQ ID NO: 8 |
| TD-AU | CAGTACTATCGGACCACAACTGCCAGACGAS | EQ ID NO: 11 |
| TD-AL | TGGTCCATCCTCCTGTATAACCCGA | SEQ ID NO: 12 |
| TD-BU | AAAACACCACGTCGTCCCTGGCT | SEQ ID NO: 13 |

TABLE 1-continued

Sequence of Primers used in the present invention

| Primer | Sequence (5'-3') | |
|---|---|---|
| TD-BL | CTCATCAAATGTCAGGATGAACAGCGTC | SEQ ID NO: 14 |
| r52UR | AGTGGTCAGATGCCCATCAAACGG | SEQ ID NO: 15 |
| r52LR | CGTTTGCTTGTGGGTTGTCACGTAG | SEQ ID NO: 16 |
| H19UR | AGCTTGCAGCCTTGCACAGTCCAG | SEQ ID NO: 17 |
| H19LR | ATGGCCCACACAGTGACCATCGGA | SEQ ID NO: 18 |
| H74UR | GATAAAGTGGTCATCAAGTACGCATTCC | SEQ ID NO: 19 |
| H74LR | GTACTTTCCGATCCGGGTCATCTC | SEQ ID NO: 20 |
| H99UR | CTTTGTTTTGATGAGCGGTCGCTT | SEQ ID NO: 21 |
| H99LR | GGTTCGTGGAGGATATCATTGCTACA | SEQ ID NO: 22 |
| H158UR | AGCCAGCACCCAGAGCATCGAACA | SEQ ID NO: 23 |
| H158LR | TCCCTTGAACAGCAGCAGGAGGCA | SEQ ID NO: 24 |

Construction of the Transformant

Although it is thought that the duplication of the chromosome occurs during a repairing step of the double-strand break of the chromosome, its mechanism has not yet been revealed. On the other hand, it was already reported that the repeated sequences were found with a high frequency at a boundary region of the duplicated region on the chromosome by analysis of the yeast obtained by means of γ-ray radiation (Non Patent Literature 1). It was therefore considered that the chromosome could be duplicated by preparing a construct wherein the targeted region to be duplicated was sandwiched between 5' ΔpyrG and 3' ΔpyrG both of which have a homologous region, and inducing the double-strand break within said homologous region (FIG. 1). Accordingly, a basic unit shown in FIG. 2 was first made for preparing the 5' ΔpyrG and 3' ΔpyrG.

The 5' ΔpyrG and 3' ΔpyrG units were prepared by means of PCR and ligation. The preparation of these ΔpyrG units was carried out by inserting the homologous sequence shown with hatched lines in FIG. 2, which may comprise the recognition site for an appropriate restriction enzyme, around an transcription initiation point of the full length of pyrG (5' ΔpyrG) or around the 3' of the coding region (3' ΔpyrG). After each of these vectors had been integrated into the chromosome, selection of 5FOA-resistant strain (negative selection) was made to give a strain comprising the 5' ΔpyrG or 3' ΔpyrG unit wherein an internal part has been excised due to the recombination within the homologous region.

Figure 3:
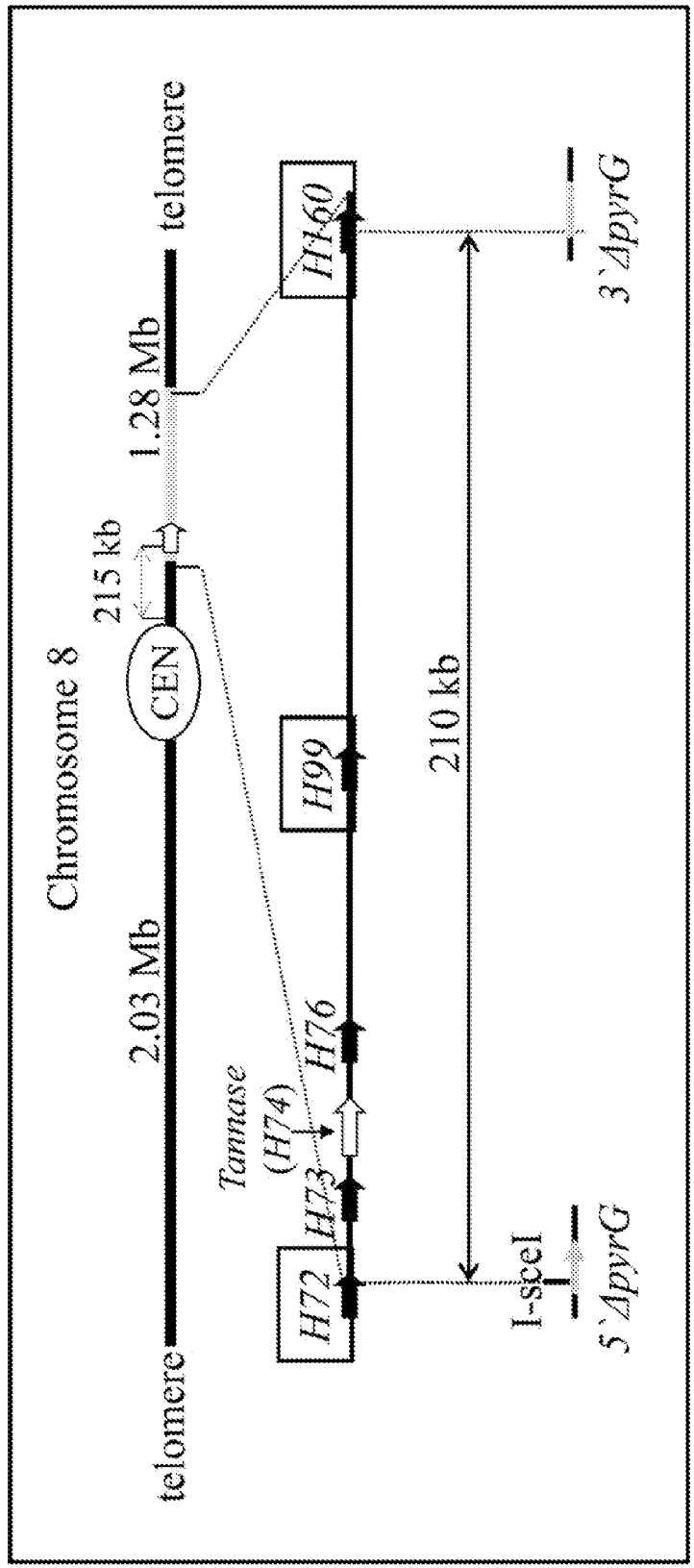
FIG. 3 shows a target region for duplication in the 8$^{th}$ chromosome.

Next, a vector for the integration of each of the 5' DpyrG and 3' DpyrG units to a targeted region to be duplicated was constructed. The targeted region was a 210 kb region corresponding to the region comprising A00901030000072~A00901030000160 genes in SC103 region of the 8$^{th}$ chromosome of *Aspergillus oryzae* (FIG. 3). Just for the purpose of simplification, the part of "A0090103000" of each gene is hereinafter abbreviated just to "H", for example "A00901030000160" is abbreviated into "H160." The SC103 region and sequence of the genes contained therein was based on the genome analysis database of National Institute of Technology and Evaluation (NITE), DOGAN (Database Of the Genomes Analyzed at NITE) (www.bio.nite.go.j/dogan/GeneMap?GENOME_ID=ao_G2). A vector (pH72-5'D) for the integration of the 5' DpyrG construct into the H72 region on the chromosome and a vector (pH160-3' D) for the integration of the 3' DpyrG construct into the H160 region on the chromosome were constructed as follows. The regions of H72 and H160 correspond to the ORF regions of A0090103000072 and A0090103000160, respectively. Regions of about 3 kb comprising H72 and H160, respectively, were amplified from the genomic DNA of *Aspergillus oryzae* with PCR using the primer H72U and H72L, and H160U and H160L, respectively, followed by cloning into a vector. A vector comprising H72 amplified by using the primers H72iU and H72iL was ligated with the 5' DpyrG unit that had been amplified by using the primers pyrU and pyrL and phosphorylated to give the vector pH72-5' D for the integration of the 5' DpyrG construct into the H72 region on the chromosome. A vector comprising H160 amplified by using the primers H160iU and H160iL was then ligated with the 3' DpyrG unit that had been amplified by using the primers pyrU and pyrL and phosphorylated to give the vector pH160-3' D for the integration of the 3' DpyrG construct into the H160 region on the chromosome.

*Aspergillus oryzae*, ΔpyrG strain (ku70+ strain) was first transformed with the vector pH72-5'Δ for the integration of the 5' Δ pyrG construct into the H72 region. Eleven strains of the resulting transformants were examined with PCR and Southern hybridization to confirm that the vector had been integrated into the targeted site in one of the strain. About $1 \times 10^5$ of conidium collected from the one strain was applied on the CZ medium plate containing 5FOA. The resulting 5FOA-resistant strain was analyzed to confirm that it contained 5'Δ pyrG construct at the H72 region (site). This strain was subjected as a parent strain to transformation with the vector pH160-3' Δ for the integration of the 3' ΔpyrG construct into the H160 region. A strain wherein the vector had been integrated into the H160 region was selected by means of PCR and Southern hybridization. Conidium collected from the selected strain was applied on the CZ medium plate containing 5FOA. The resulting 5FOA-resistant colony was analyzed to confirm the construction of a strain (F5 strain) wherein the 5' Δ pyrG construct was integrated into the H72 site that was located most closely to centromere in the target region to be duplicated (210 kb region) and the 3' Δ pyrG construct was integrated into the H160 site that was located closely to telomere in said region the most. Thus, the F5 strain having a basic structure for the duplication of the 210 kb region on the 8$^{th}$ chromosome was successfully constructed. It was revealed that the middle portion with about 500 bp of the coding region existed in common in the transformation marker genes with the deficiency of its parts, which were integrated into the 8$^{th}$ chromosome of the transformant Construction of the Transformant Having the Chromosome Duplication The experiment of duplication of the chromosome was done using the above F5 strain. I-secI was used at 0 U and 30 U, respectively to give one pyrG+ colony from each plate. Chromosomal DNA was then extracted from the resulting two pyrG+ strains (0C strain and 50B strain) and subjected to PCR, Southern hybridization and the quantitative PCR (real-time PCR) in order to confirm the duplication of the chromosome.

Figure 4:
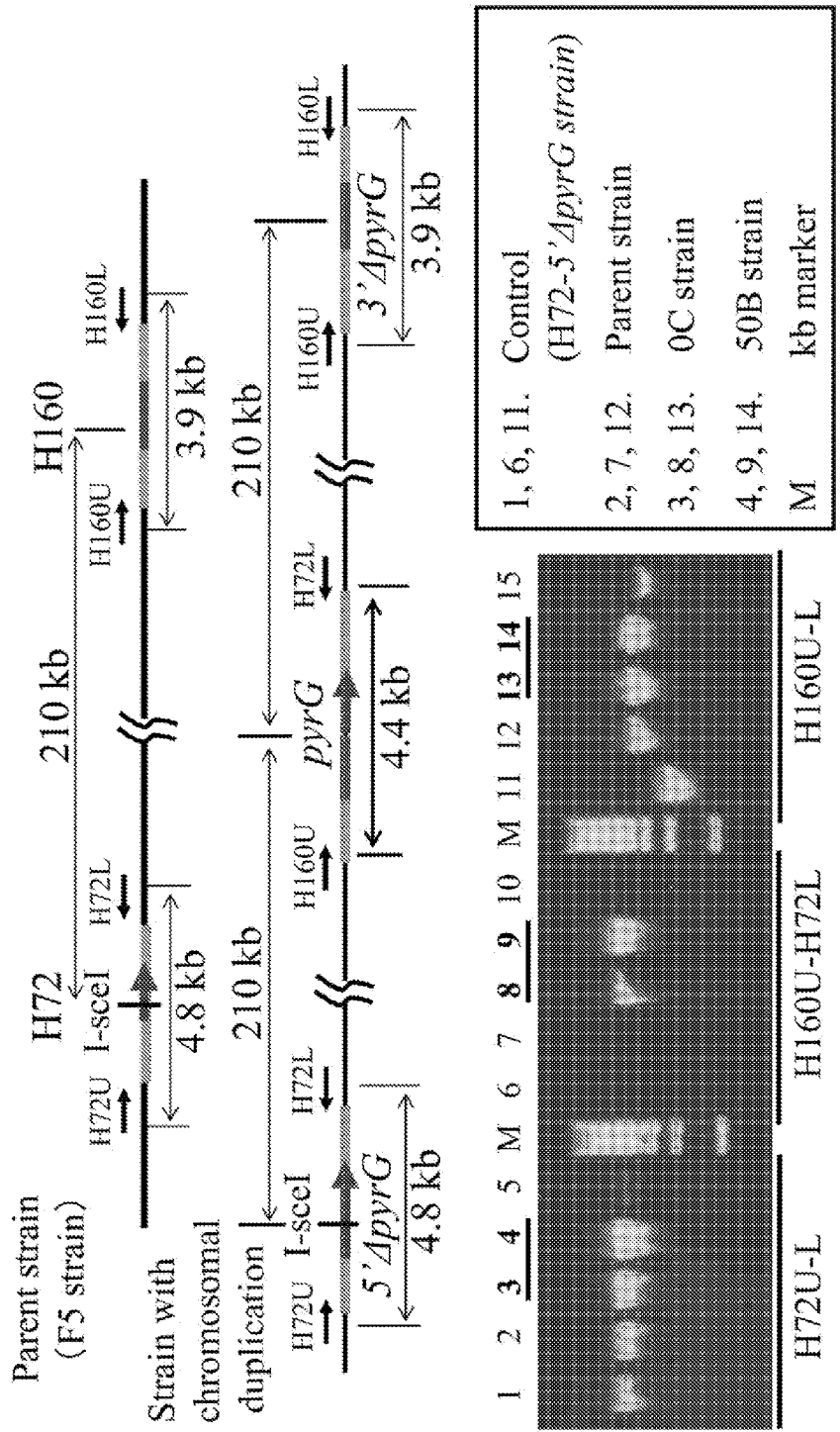
FIG. 4 shows the results of PCR.

The results of PCR are shown in FIG. 4. In the case of using a pair of the primers (H72U and H72L, and H160U and H160L) in the PCR for amplification of H72 and H160 at both ends of the region to be duplicated, bands of 4.8 kb and 3.9 kb were amplified both in a control strain and a strain having the chromosome duplication. On the other hand, use of a pair of the primers H160U-H72L did not show any amplification of a band in the control or parent strain, but clearly showed the amplification of a band of 4.4 kb in the strain having the chromosome duplication (0C strain and 50B strain). Since it was considered that this band could be obtained only when the chromosomal region had been duplicated, it was thought that these results did demonstrate that the region of 210 kb between H72 and H160 on the 8$^{th}$ chromosome had been duplicated in the 0C and 50B strains.

Figure 5:
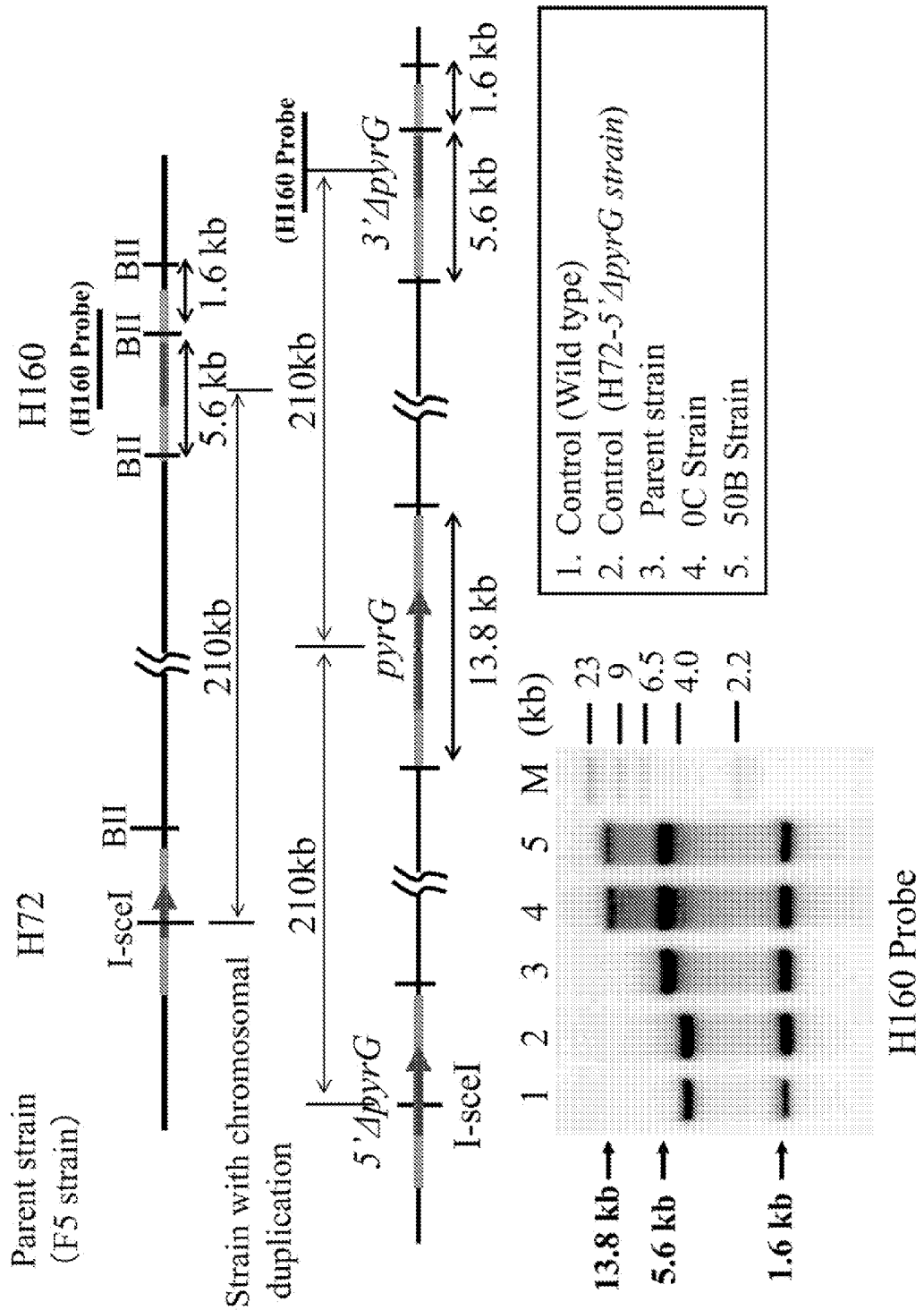
FIG. 5 shows the results of Southern hybridization.
Figure 6:
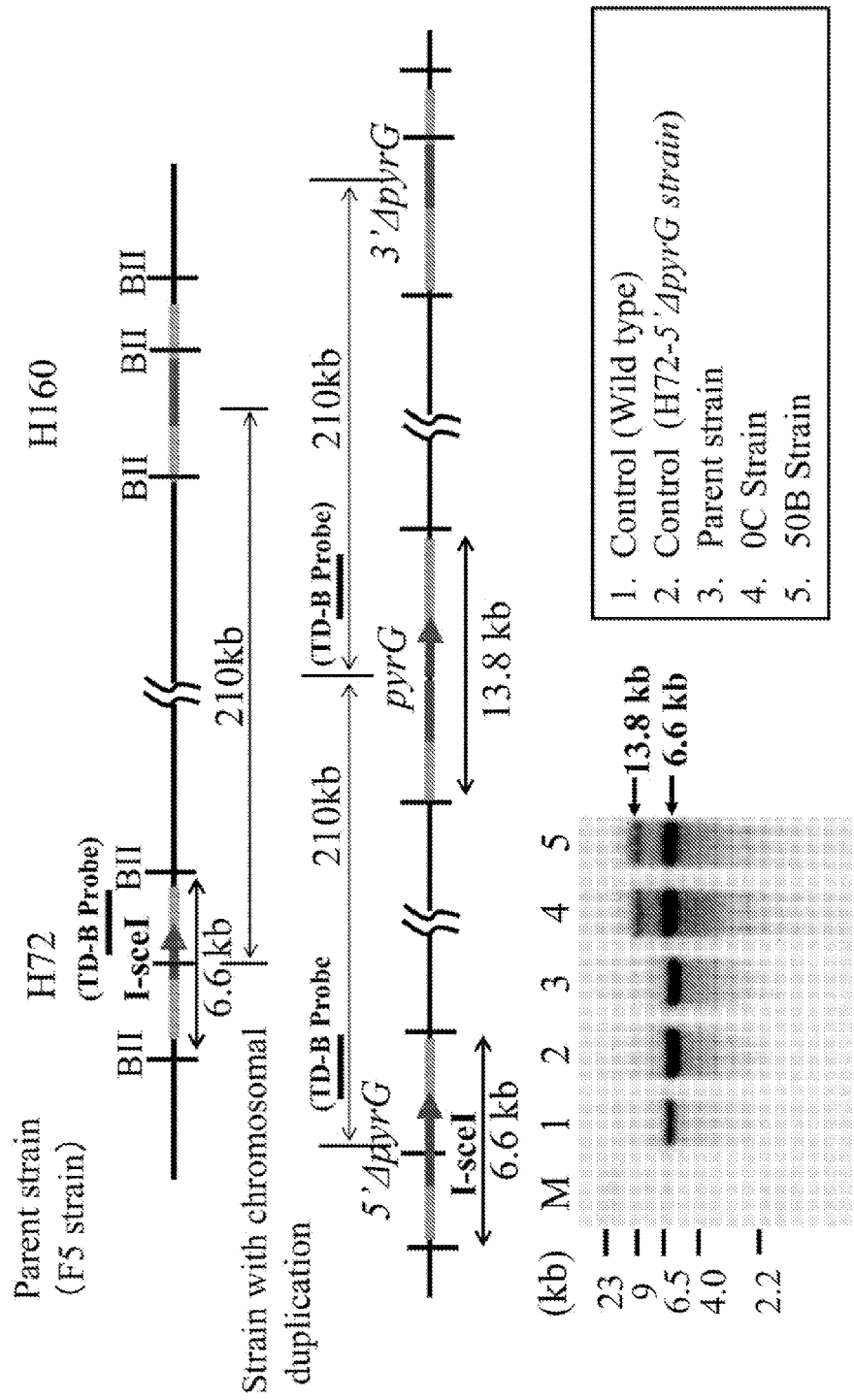
FIG. 6 shows the results of Southern hybridization.
Figure 7:
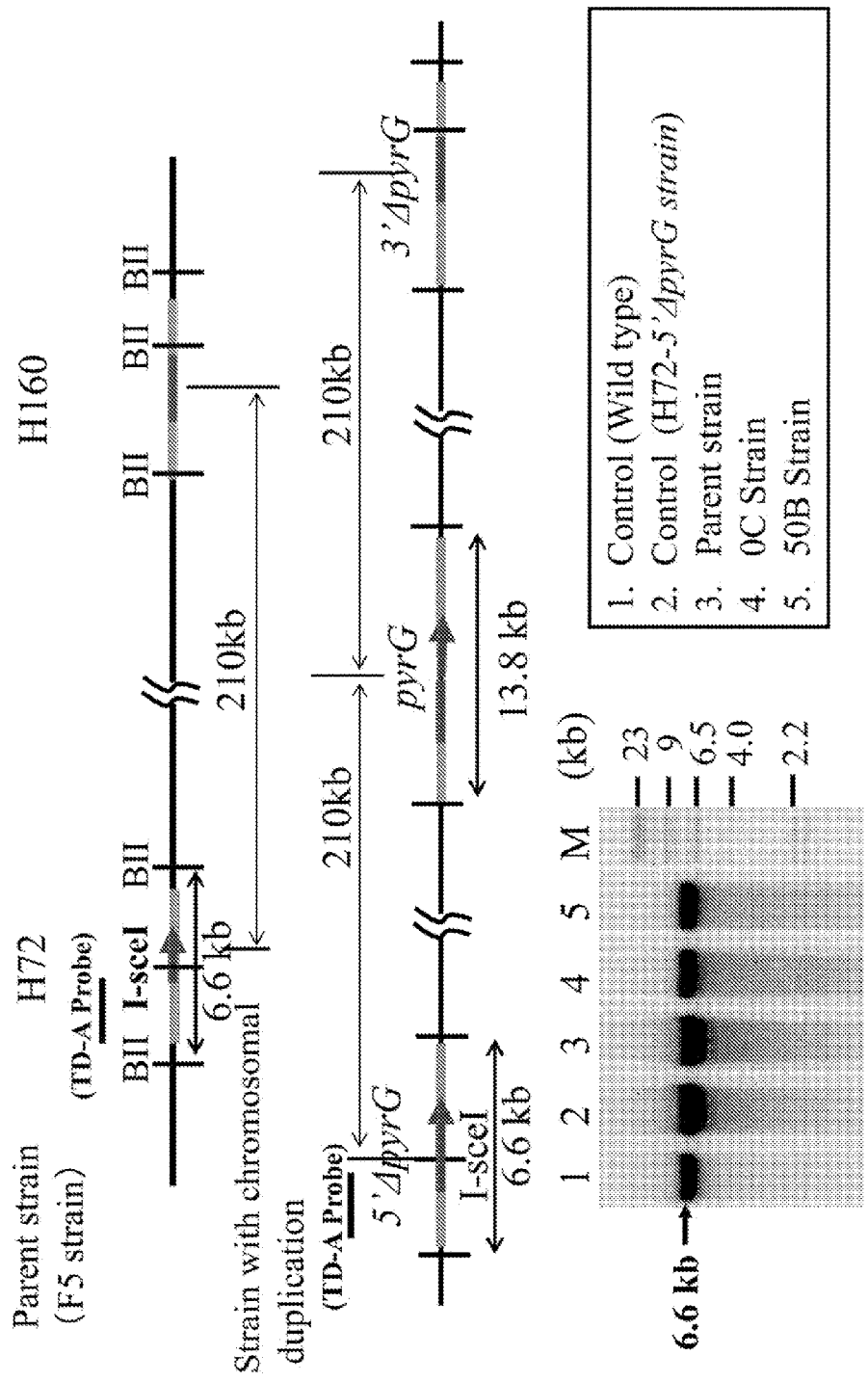
FIG. 7 shows the results of Southern hybridization.

The results obtained in Southern hybridization are then shown in FIGS. 5~7. Genomic DND was digested with BgIII and hybridized with a H160 probe located at the end of the region to be duplicated.

The upper part of the FIG. 5 shows a restriction enzyme map and the location of probes of the target region to be duplicated on the 8$^{th}$ chromosome of the parent strain and the strain having the chromosome duplication. It was then expected that the H160 probe would give only two bands of 5.6 kb and 1.6 kb in the parent strain. On the other hand, it was considered that a new band of 13.8 kb comprising a full-type pyrG would be also generated by using the H160 probe if the region had been duplicated on the 8$^{th}$ chromosome as just expected. According to the results in FIG. 5, while the two bands were observed in the control and parent strains (Lanes 1~3), an additional band was recognized also at 13.8 kb in the two strains having the chromosome duplication (Lanes 4 and 5). These results supported the fact that the region had been duplicated to on the 8$^{th}$ chromosome as just expected.

Next, the Southern hybridization was carried out using the same membrane and a TD-B probe located around H72 at the end of the region to be duplicated (FIG. 6). While only a band of 6.6 kb was observed in the control and parent strains (Lanes 1~3), an additional band of 13.8 kb was also recognized in the two strains having the chromosome duplication (Lanes 4 and 5), showing that these data also supported the fact that the region had been duplicated on the 8$^{th}$ chromosome as just expected.

Figure 8:
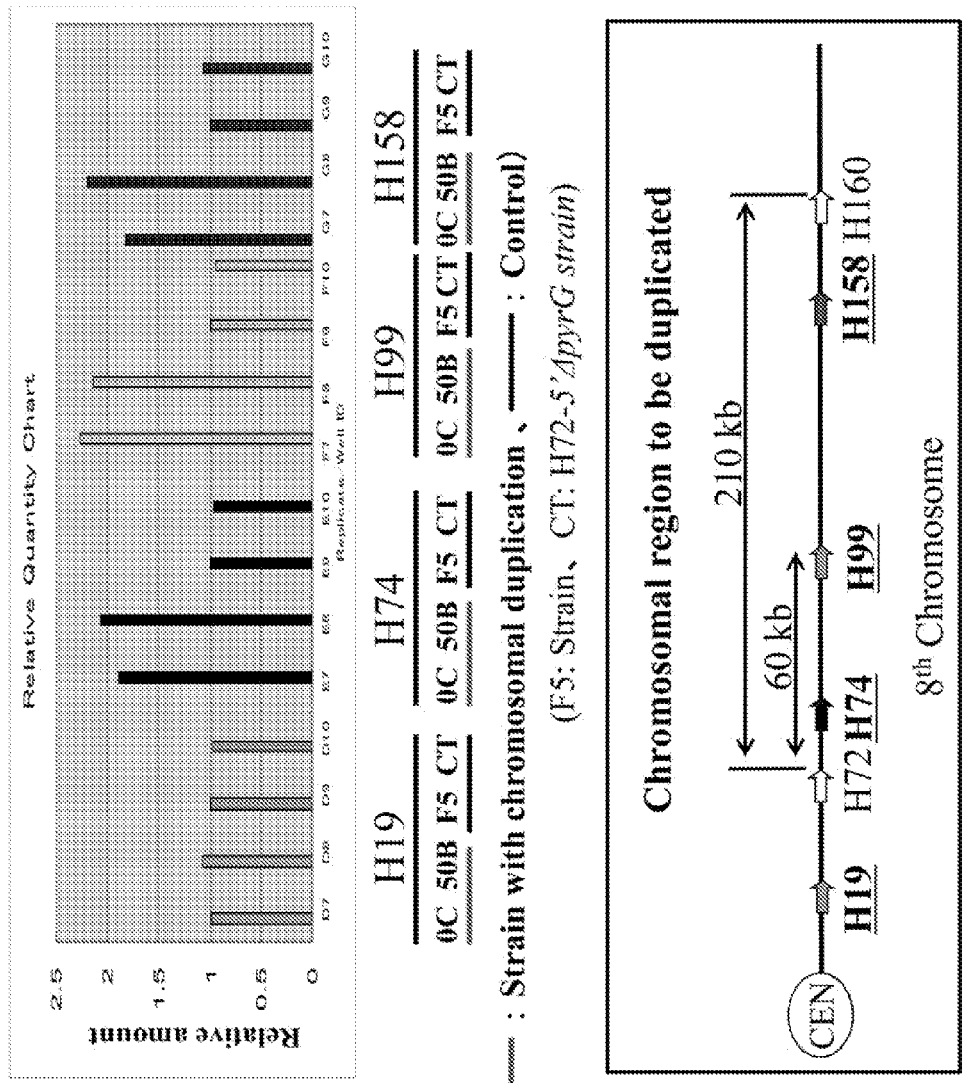
FIG. 8 shows the numbers of copies of each gene in the duplicated region of the $8^{th}$ chromosome, which was obtained by a quantitative PCR.

On the other hand, only the band of 6.6 kb was observed in the same way among the control, parent and strain having the chromosome duplication when the Southern hybridization was carried out with a probe TD-A located outside the duplicated region (FIG. 7), The numbers of copies of each gene in the duplicated region of the 8$^{th}$ chromosomes were compared between the control strain and the strain having the chromosome duplication by means of the quantitative PCR (FIG. 8) with SYBR Green. The comparison was made by means of the relatively quantitative method using rad52 as a mormalizer, which was also present in other chromosomes and its number of copy is one, with respect to H74 gene (tannase) located at the end of the centromere side in the duplicated region, H99 gene located apart from the H74 gene by 60 kb, H158 gene located at the end of the telomere side in the targeted region, and H19 gene located outside of the duplicated region. As a result, a value of about one (1) was indicated with respect to all of the H19, H74, H99 and H158 genes in the control strains (F5 and CT strains) to show that their number of copies is one. On the other hand, while the value of about one (1) was indicated with respect to the H19 gene located outside the duplicated region in the strains having the chromosome duplication (0C strain and 50B strain), values of about 2 or more were indicated in these strains with respect to the H74, H99 and H158 genes located within the duplicated region to confirm that copies of these genes were amplified twice or more in said strains.

It was confirmed that the targeted 210 kb region on the 8$^{th}$ chromosome had been actually duplicated in the 0C and 50B strains just as expected by the results obtained in PCR, Southern hybridization and the quantitative PCR.

EXAMPLE 2

Next, a transformant with duplication of the $2^{nd}$ chromosome was constructed. The matters not described below (strain, culture medium, transformation, construction of a transformant with duplication of chromosome and the like) were done in the same way as in Example 1.

METHODS

Comparison of the Numbers of Gene Copies in the Chromosome by Means of Quantitative PCR (Real-Time PCR)

The quantitative PCR was carried out using Mx3005P (Agilent Technologies). The numbers of copies of Alp, amyR, prtT and 1258D genes in the $2^{nd}$ chromosome were compared between the parent strain and the strains having duplicated chromosomes by means of the relatively quantitative method with the rad52 present in the other chromosome as the mormalizer. The PCR was first kept for ten min., at 95° C., followed by repeating 45 times a cycle of heating for 20 seconds at 95° C., for 30 seconds at 58° C. and for 30 seconds at 72° C. The genes of Rad52, Alp, amyR, prtT and 1258D were amplified using the primers of r52U-r52L, amyRU-amyRL, AlpU-AlpL, prtTU-prtTL and 1258DU-1258DL, respectively (Table 2).

TABLE 2

Table 2 Sequences of Primers used in Real-time PCR

| primer | sequence (5'-3') | | |
|--------|------------------|---|---|
| r52UR | AGTGGTCAGATGCCCATCAAACGG | SEQ ID NO: | 15 |
| r52LR | CGTTTGCTTGTGGGTTGTCACGTAG | SEQ ID NO: | 16 |
| Alp-U | TTGAGCGCAACTACAAGATCAAC | SEQ ID NO: | 25 |
| Alp-L | GGTAGTCAGGCCATCGAGGTAGT | SEQ ID NO: | 26 |
| Amy-U | CCACGCACATCCAACTGAAG | SEQ ID NO: | 27 |
| Amy-L | GTCGACCACGTTGTATTCCTTTC | SEQ ID NO: | 28 |
| prtT-U | AATTCAGGACCTCCAATCTGAGT | SEQ ID NO: | 29 |
| prtT-L | GATGGACATGACGAGTGACCATA | SEQ ID NO: | 30 |
| 1258D-U | CAGCTTTATCACTTTGGGAGCTG | SEQ ID NO: | 31 |
| 1258D-L | TGAGTTTGGCAGACTATAGGCAAG | SEQ ID NO: | 32 |

Preparation of Wheat-Bran Koji Mold (*Aspergillus* Strain)

The enzyme activity of *Aspergillus* strain was carried out in a conventional manner. Thus, wheat bran with sprayed to 80% water (5 g) was placed into a conical flask (150 ml) and sterilized for 50 min. at 121° C. To this was inoculated two platinum loops of the *Aspergillus* strain and cultured for 4 days at 30° C. The culture was then mixed with 100 ml of sterilized water, sealed with a rubber plug, sufficiently shaken, allowed to stand for 4 hours at a room temperature and filtered with paper filter No. 2 (Advantech Co.) to give an extract solution, which was used as an enzyme sample.

Determination of Protease Activity

The resulting enzyme sample was appropriately diluted, and determined by a method described in "Soy sauce test method" (Japan Soysauce Institute, Showa 60 (1985), p. 287).

The protease activity was indicated with a titer of "1 U" that could generate 1 μmol of tyrosine for one minute per 1 g of wheat bran koji mold.

Determination of α-Amylase Activity

The resulting enzyme sample was appropriately diluted, and subjected to determination with α-amylase determination kit (Kikkoman brewing analysis kit, code 60213) in accordance with a protocol of the kit. The α-amylase activity was shown with a titer of "1 U" that could release 1 μmol of 2-chloro-4-nitrophenol for one minute per 1 g of wheat bran koji mold.

Construction of the transformant

Figure 9:
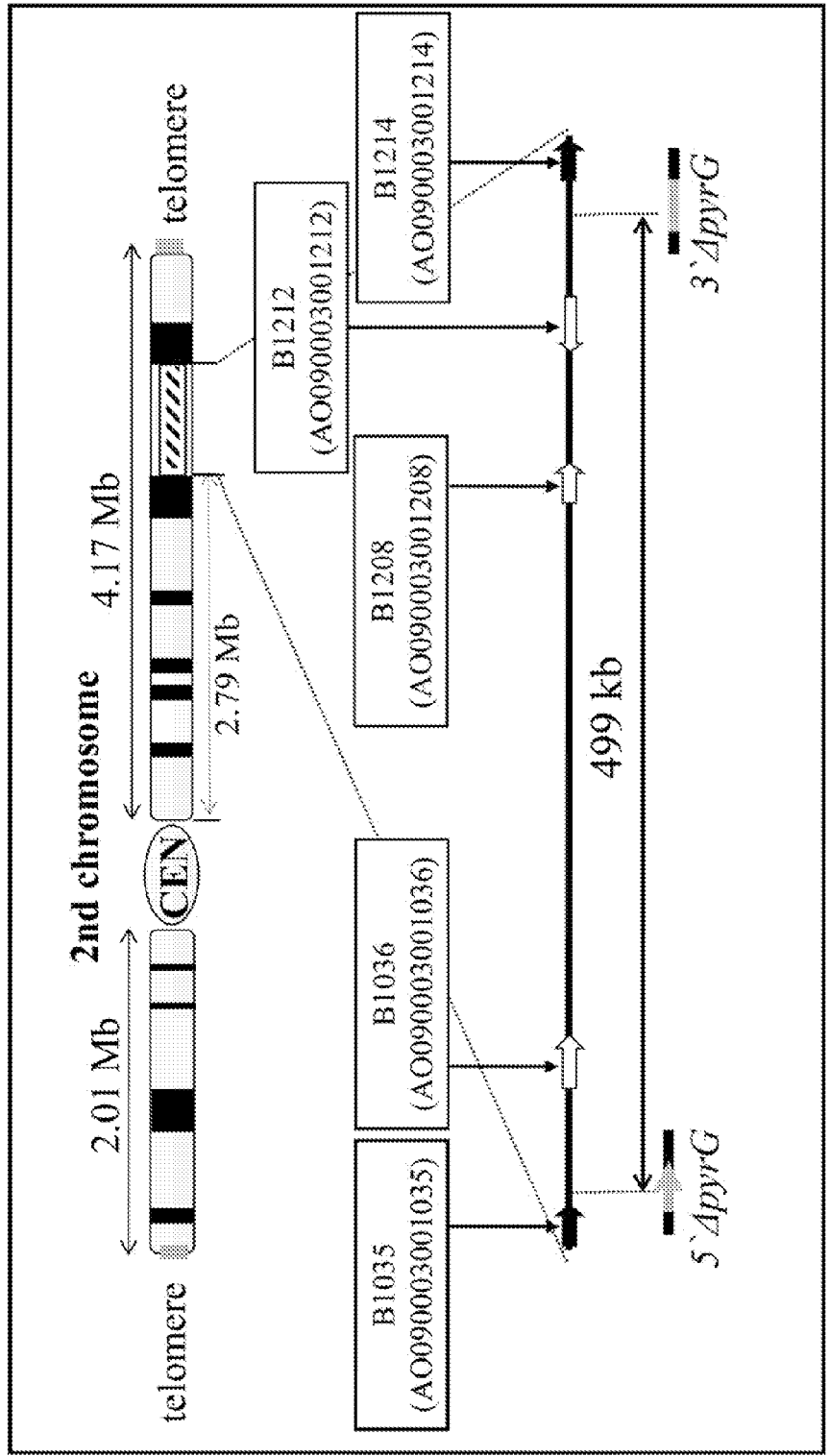
FIG. 9 shows a target region for duplication in the 2nd chromosome.

Next, a vector for the integration of each of the 5' DpyrG and 3' DpyrG units to a targeted region to be duplicated was constructed. The targeted region was a 499 kb region corresponding to the region comprising A0090003001036~A0090003001212 genes in SC003 region of the 2nd chromosome of *Aspergillus oryzae* (FIG. 9, shown with hatched lines). Just for the purpose of simplification, the part of "A0090003000" of each gene is abbreviated just to "B" in this Example, for example "A0090003000160" is abbreviated into "B160.". The SC003 region and sequence of the genes contained therein was based on the genome analysis database of NITE, DOGAN (Database Of the Genomes Analyzed at NITE) (www.bio.nite.go.j/dogan/GeneMap?GENOME_ID=ao_G2).

A vector (pB1035C-5' Δ) for the integration of the 5' ΔpyrG construct between B1035 and B1036 on the chromosome and a vector (pB1213C-3' A) for the integration of the 3' ΔpyrG construct between B1212 and B1214 on the chromosome were constructed as follows.

The regions of B1035, B1036, B1212 and B1214 correspond to the ORF regions of A0090003001035, A0090003001036, A0090003001212 and A0090003001214, respectively. Regions of about 3 kb comprising the middle region between B1035 and B1036, and the middle region between B1212 and B1214, respectively, were amplified from the genomic DNA of *Aspergillus oryzae* with PCR using the primer B1035CU and B1035CL, and B1213CU and B1213CL, respectively, followed by cloning into a vector.

A vector comprising the middle region between B1035 and B1036 amplified by using the primers B10351U and B10351L was ligated with the 5' ΔpyrG unit that had been amplified by using the primers pyrU and pyrL and phosphorylated to give the vector pB1035C-5' Δ for the integration of the 5' ΔpyrG construct into the middle region between B1035 and B1036 on the chromosome. A vector comprising the middle region between B1212 and B1214 amplified by using the primers B12131U and B1213iL was then ligated with the 3' ΔpyrG unit that had been amplified by using the primers pyrU and pyrL and phosphorylated to give the vector pB1213C-3' Δ for the integration of the 3' ΔpyrG construct into the middle region between B1212 and B1214 on the chromosome.

*Aspergillus oryzae*, ΔpyrG strain (ku70+ strain) was first transformed with the vector pB1035C-5' a for the integration of the 5' ΔpyrG construct into the middle region between B1035 and B1036. The resulting transformants were examined with PCR and Southern hybridization to confirm that said vector had been integrated into the targeted site in one of the strains. About 1×10⁵ of conidium collected from the one strain was applied on the CZ medium plate containing 5FOA. The resulting 5FOA-resistant strain was analyzed to confirm that it contained 5'Δ pyrG construct in the middle region between B1035 and B1036. This strain was subjected as a parent strain to transformation with the vector pB1213C-3' Δ for the integration of the 3' ΔpyrG construct into the middle region between B1212 and B1214. A strain wherein the vector had been integrated into the middle region between B1212 and B1214 was selected by means of PCR and Southern hybridization. Conidium collected from the selected strain was applied on the CZ medium plate containing 5FOA, and the resulting 5FOA-resistant colonies were analyzed to confirm the construction of a strain (C-4-hap strain) wherein the 5' Δ pyrG construct was integrated into the middle region between B1035 and B1036 that was located most closely to centromere in the target region to be duplicated (499 kb region) and the 3' Δ pyrG construct was integrated into the middle region between B1212 and B1214 that was located most closely to telomere in said region. Thus, the C-4-hap strain having a basic structure for the duplication of the 499 kb region on the 2nd chromosome was successfully constructed (FIG. 9). The primers used in the construction of the transformant having duplication were shown in Table 3. It was revealed that the middle portion with about 500 bp of the coding region existed in common in the transformation marker genes with the deficiency of its parts, which were integrated into the $2^{nd}$ chromosome of the transformant.

TABLE 3

Table 3 Sequencesof primers used in the construction of the transformant with duplication

| primer | sequence (5'-3') |
|---|---|
| B1035-CU | AGCAACCCAAGTGCGAAGCCTATCGAG |
| B1035-CL | GAATCCAGTTGAGTCGGAGCACCGCA |
| B1035-iU | GGCAGCGGTTACAGGTAAGCTCCCAATGCAAACAAGACAAA |
| B1035-iL | ACATCACAGGGTAGGTCCAATAAACATGGCCACTTTTCAGTT |
| B1213-CU | CCGAAATCCAAAAGTAGCCTGTAGTC |
| B1213-CL | CACCTGAGTAGGGCTGTATTTGAAAC |
| B1213-iU | GGCAGCGGTTACAGGTAGACTTGCAGAAGATACCCAACTG |
| B1213-iL | ACATCACAGGGTAGGGTTTGTTCCAACGGCATAAGGAC |
| pyrU | CCTACCCTGTGATGTTCATCACTAATGCC |
| PyrL | CTGTAACCGCTGCCTCATTTCCCACAGGTT |

Construction of the Transformant Having the Chromosome Duplication

The experiment of duplication of the chromosome was done in accordance with the method mentioned above using the above C-4-hap strain. Chromosomal DNA was then extracted from the resulting one pyrG+ colony (C-4-499k strain) obtained in the regeneration plate and subjected to PCR and the quantitative PCR (real-time PCR) in order to confirm the duplication of the chromosome.

Figure 10:
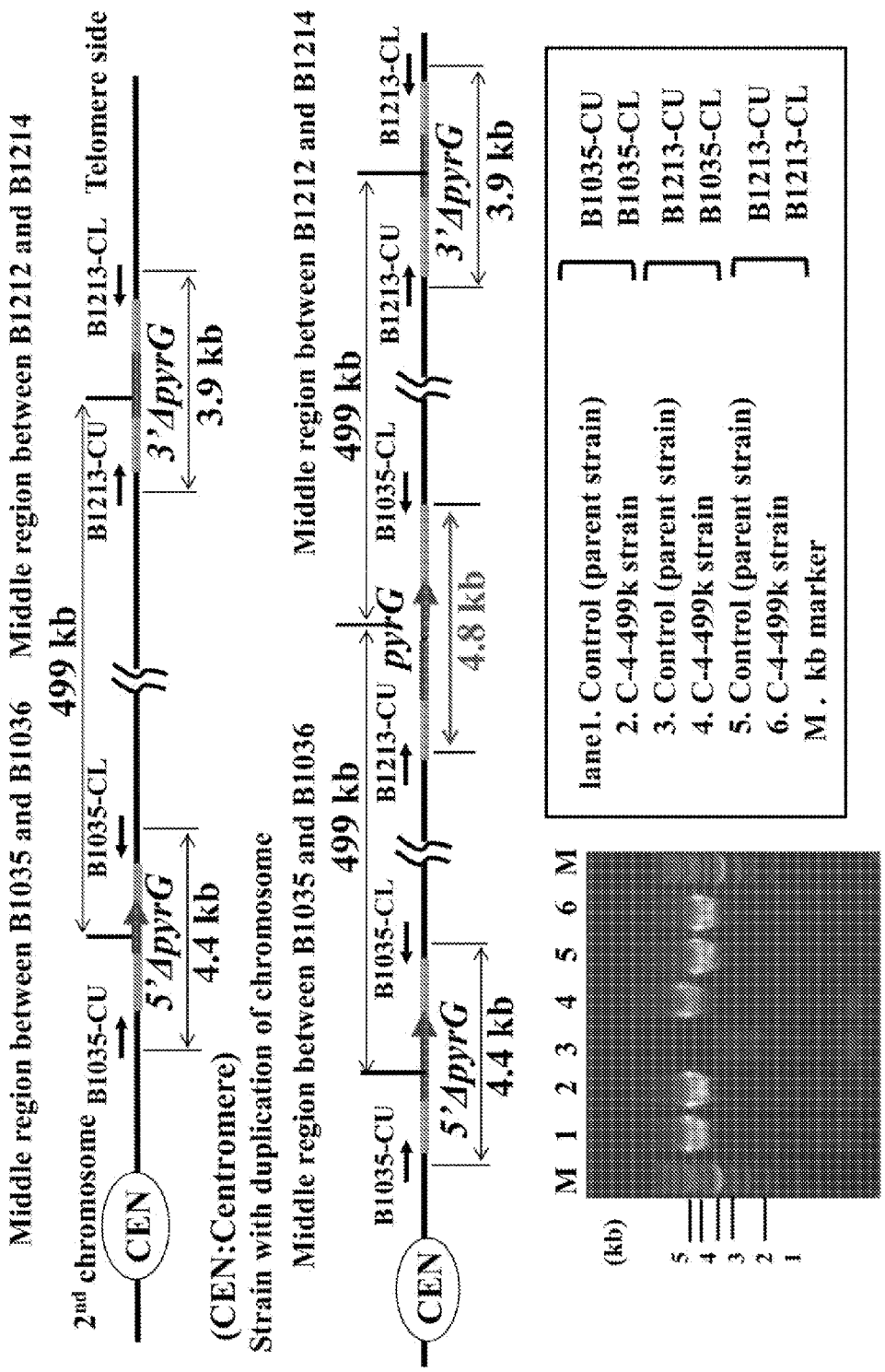
FIG. 10 shows the results of PCR.

The occurrence of the duplication of the chromosome was first confirmed with PCR. The results of PCR are shown in FIG. 10. In the case of using a pair of the primers (B1035CU and B1035CL) in the PCR for amplification of the middle region between B1035 and B1036 that contained the integrated vector pB1035C-5' Δ and was located most closely to centromere (FIG. 10 upper), a band of 4.4 kb was amplified both in a control strain (a parent strain: C-4-hap strain) and the strain (C-4-499k strain) having the chromosome duplication (FIG. 10, lower, Lanes 1 and 2). In the case of using a pair of the primers (B1213CU and B1213CL) in the PCR for amplification of the middle region between B1212 and B1214 that contained the integrated vector pB1213C-3' Δ and was located most closely to telomere (FIG. 10 upper), a band of 3.9 kb was amplified both in the control strain and the strain (C-4-499k strain) having the chromosome duplication (FIG. 10, lower, Lanes 5 and 6). On the other hand, use of a pair of the primers B1213CU-B1035CL (FIG. 10 middle) did not show any amplification of a band in the control strain, but clearly showed the amplification of a band of 4.8 kb in the strain having the chromosome duplication. Since it was considered that this 4.8 kb band could be obtained only when the chromosomal region had been duplicated, it was thought that these results did demonstrate that the region of 499 kb between B1035 and B1212 on the $2^{nd}$ chromosome had been duplicated in the C-4-499k strain.

Figure 11:
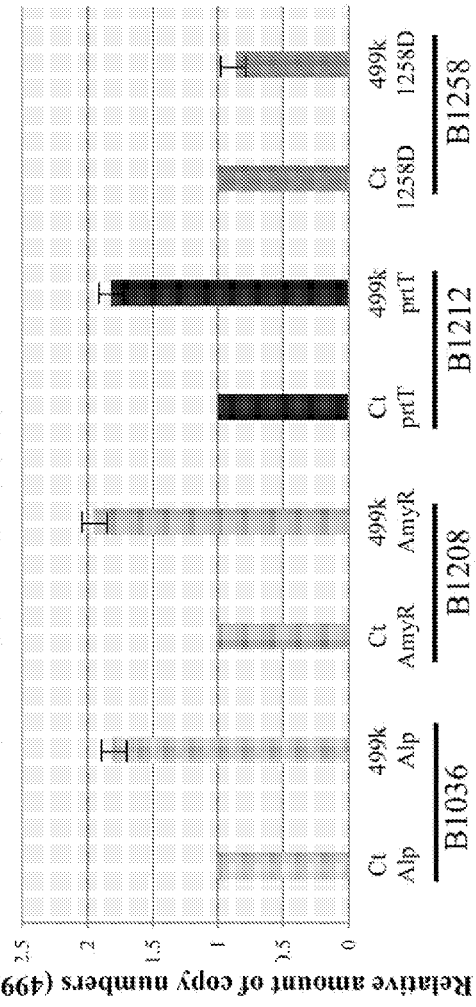
FIG. 11 shows the numbers of copies of each gene in the duplicated region of the 2nd chromosome, which was obtained by a quantitative PCR.
Figure 11:
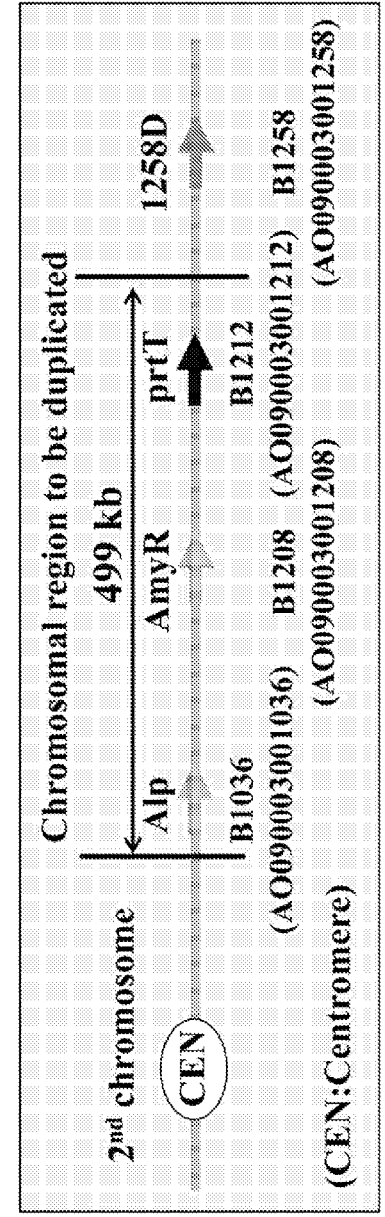

The numbers of copies of each gene in the duplicated region of the $2^{nd}$ chromosomes were compared between the control strain (the parent strain: C-4-hap strain) and the C-4-499k strain having the chromosome duplication by means of the quantitative PCR with SYBR Green (FIG. 11). The comparison was made by means of the relatively quantitative method using rad52 as a mormalizer, which was also present in other chromosomes and its number of copy is one, with respect to B1036 gene (Alp) located at the end of a centromere side in the duplicated region, B1208 gene (amyR) located apart from the B1036 gene by 490 kb, B1212 gene (prtT) located at the end of a telomere side in the targeted region, and B1258D gene located outside of the duplicated region. As shown in FIG. 11, while a value of about one (1) was indicated with respect to the B1258D gene located outside the duplicated region in the strain having the chromosome duplication (C-4-499k strain), values of about 2 were indicated in the strain with respect to the B1036, B1208 and B1212 genes located within the duplicated region to confirm that copies of the these genes were amplified twice in said strain.

It was confirmed that the targeted 499 kb region on the 2nd chromosome had been actually duplicated in the C-4-499k strain just as expected by the results obtained in PCR and the quantitative PCR.

Patent Literature 1 reported that a remarkable increase of the protease activity and amylase activity was observed in the strain having the duplication of genomic region corresponding to the region of A0090003001003~A0090003001259 genes in SC003 of the 2nd chromosome of *Aspergillus oryzae*. The above activities were therefore determined with respect to the strain having the 2nd chromosome duplication obtained in this Example. A D-2-695k strain was used as a control, wherein 695 kb region corresponding to the region of A0090003001003~A0090003001258 genes (B1003~B1258) of the 2nd chromosome of *Aspergillus oryzae*.

Results of Determination of Protease Activity

Figure 12:
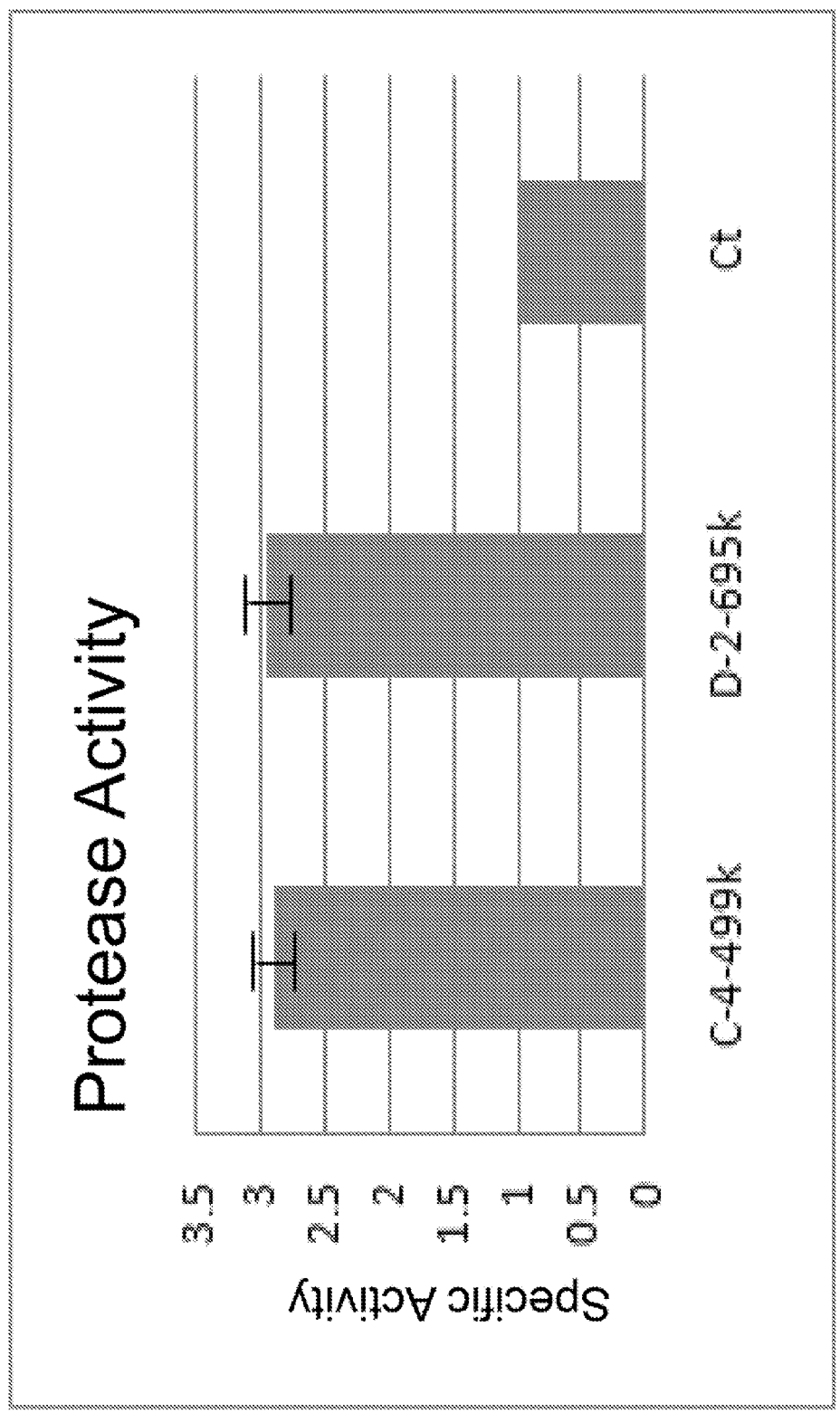
FIG. 12 shows the results of determination of protease activity.

Determination of a total protease activity was done using the enzyme extract obtained from the wheat-bran koji mold according to the method mentioned above so as to compare it between the parent strain and the strain having the duplication. The results are shown in FIG. 12. The protease activity had been increased about three times higher in the C-4-499k strain than in the parent strain, which was almost the same increase level obtained in the D-2-695k strain. Accordingly, it was confirmed that the C-4-499k strain with the duplication of 499 kb according to the present invention showed the increase in the protease activity in the wheat-bran culture, which is similar to that of the D-2-695k strain with the duplication of 695 kb.

Results of Determination of α-Amylase Activity

Figure 13:
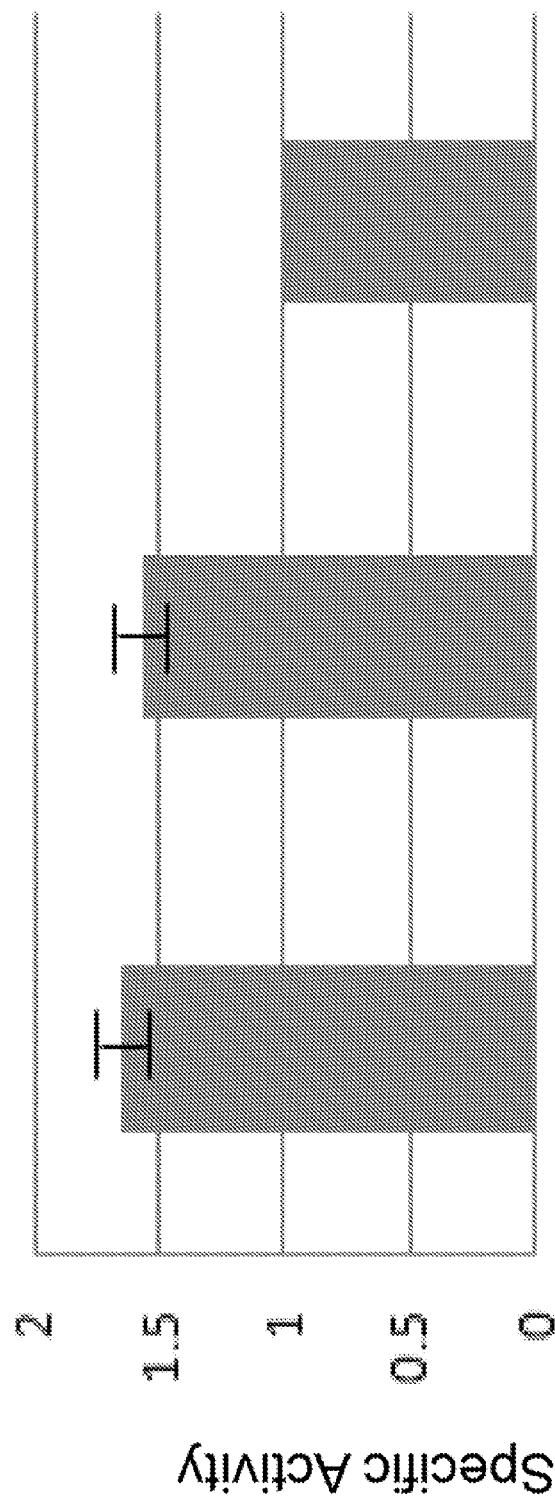
FIG. 13 shows the results of determination of α-amylase activity.

Determination of α-amylase activity was done using the same enzyme extract as above so as to compare it between the parent strain and the strain having the duplication. The results are shown in FIG. 13. The α-amylase activity had been increased about 1.6 times higher in the C-4-499k strain than in the parent strain, which was almost the same increase level obtain in the D-2-695k strain. Accordingly, it was confirmed that the C-4-499k strain with the duplication of 499 kb according to the present invention showed the increase in the α-amylase activity in the wheat-bran culture, which is similar to that of the D-2-695k strain with the duplication of 695 kb.

The above results confirmed that the targeted 499 kb region on the 2nd chromosome had been actually duplicated in the C-4-499k strain, and that a remarkable increase of the protease activity and amylase activity was observed in said strain like the strain having 695 kb duplication. According, it has been demonstrated that the duplication of such a shorter region as that of 499 kb region comprising B1036~B1212 on the $2^{nd}$ chromosome would be enough for the increase of protease activity and amylase activity.

INDUSTRIAL APPLICABILITY

The method according to the present method has now made it possible to identify a chromosomal region considered to be important from a practical point of view based on the information about the genome of a fungus strain to be bred, and to produce a strain having the duplication of said chromosomal region. Accordingly, it is expected that an efficient molecular breeding will be developed, so as to produce *Aspergillus* strains wherein a new useful trait, which was completely unknown in the art, has been increased.

What is claimed is:

1. A recombinant *Aspergillus* fungus comprising a nucleotide sequence comprising the following elements serially in the 5' to 3' direction:
 a. a first transformation marker gene fragment with a 5' terminal deficiency located at the 5' end of a first chromosome region coding sequence;
 b. the first chromosome region coding sequence;
 c. an intact transformation marker gene;
 d. a second chromosome region coding sequence; and
 e. a second transformation marker gene fragment with a 3' terminal deficiency located at the 3' end of the second chromosome region coding sequence,
 wherein the first and second chromosome regions are identical; and the intact transformation marker gene, and the first and second transformation marker gene fragments each comprise a homologous region.

2. The recombinant *Aspergillus* fungus according to claim 1, wherein the fungus is *Aspergillus sojae* or *Aspergillus oryzae*.

3. The recombinant *Aspergillus* fungus according to claim 1, wherein the transformation marker gene is selected from the group consisting of pyrG, sC and niaD.

4. The recombinant *Aspergillus* fungus according to claim 1, wherein the first chromosome region and the second chromosome region each have a length of 200-500 kb.

5. A recombinant *Aspergillus* fungus comprising a nucleotide sequence comprising the following elements serially in the 5' to 3' direction:
 f. a first transformation marker gene fragment with a 3' terminal deficiency located in a reverse direction at the 5' end of a first chromosome region coding sequence;
 g. the first chromosome region coding sequence;
 h. an intact transformation marker gene in a reverse direction;
 i. a second chromosome region coding sequence; and
 j. a second transformation marker gene fragment with a 5' terminal deficiency located in a reverse direction at the 3' end of the second chromosome region coding sequence,
 wherein the first and second chromosome regions are identical; and the intact transformation marker gene, and the first and second transformation marker gene fragments each comprise a homologous region.

6. The recombinant *Aspergillus* fungus according to claim 5, wherein the fungus is *Aspergillus sojae* or *Aspergillus oryzae*.

7. The recombinant *Aspergillus* fungus according to claim 5, wherein the transformation marker gene is selected from the group consisting of pyrG, sC and niaD.

8. The recombinant *Aspergillus* fungus according to claim 5, wherein the first chromosome region and the second chromosome region each have a length of 200-500 kb.

* * * * *

SEQUENCE LISTING

```
<160> NUMBER OF SEQ ID NOS: 40

<210> SEQ ID NO 1
<211> LENGTH: 30
<212> TYPE: DNA
<213> ORGANISM: Artificial Sequence
<220> FEATURE:
<223> OTHER INFORMATION: Synthetic Construct; H72U

<400> SEQUENCE: 1
ttcgagatat tttcggtatc cagcaagaca                                        30

<210> SEQ ID NO 2
<211> LENGTH: 28
<212> TYPE: DNA
<213> ORGANISM: Artificial Sequence
<220> FEATURE:
<223> OTHER INFORMATION: Synthetic Construct; H72L

<400> SEQUENCE: 2
taggtactct gatacccaaa cggtcgaa                                          28

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct; H72-iU

<400> SEQUENCE: 3
agaaacacca cgtcgtccct ggct                                              24

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct; H72-iL

<400> SEQUENCE: 4
caagtccatc ctcctgtata acccga                                            26

<210> SEQ ID NO 5
<211> LENGTH: 30
<212> TYPE: DNA
<213> ORGANISM: Artificial Sequence
```

```
<220> FEATURE:
<223> OTHER INFORMATION: Synthetic Construct; H160U

<400> SEQUENCE: 5
tgtagatgca aatgattaat attcgttccc                                          30

<210> SEQ ID NO 6
<211> LENGTH: 26
<212> TYPE: DNA
<213> ORGANISM: Artificial Sequence
<220> FEATURE:
<223> OTHER INFORMATION: Synthetic Construct; H160L

<400> SEQUENCE: 6
acgtgattag aaagtacagc atcgtt                                              26

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct; H160-iU

<400> SEQUENCE: 7
cgacagactc taccgggtcg atgcc                                               25

<210> SEQ ID NO 8
<211> LENGTH: 26
<212> TYPE: DNA
<213> ORGANISM: Artificial Sequence
<220> FEATURE:
<223> OTHER INFORMATION: Synthetic Construct; H160-iL

<400> SEQUENCE: 8
ccccggatcc aagactgttg cgagtt                                              26

<210> SEQ ID NO 9
<211> LENGTH: 29
<212> TYPE: DNA
<213> ORGANISM: Artificial Sequence
<220> FEATURE:
<223> OTHER INFORMATION: Synthetic Construct; pyrU

<400> SEQUENCE: 9
cctaccctgt gatgttcatc actaatgcc                                           29

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct; pyrL

<400> SEQUENCE: 10
ctgtaaccgc tgcctcattt cccacaggtt                                          30

<210> SEQ ID NO 11
<211> LENGTH: 30
<212> TYPE: DNA
<213> ORGANISM: Artificial Sequence
<220> FEATURE:
<223> OTHER INFORMATION: Synthetic Construct; TD-AU

<400> SEQUENCE: 11
gagtactatc ggaccacaac tgccagacga                                          30
```

```
<210> SEQ ID NO 12
<211> LENGTH: 25
<212> TYPE: DNA
<213> ORGANISM: Artificial Sequence
<220> FEATURE:
<223> OTHER INFORMATION: Synthetic Construct; TD-AL

<400> SEQUENCE: 12
tggtccatcc tcctgtataa cccga                                   25

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct; TD-BU

<400> SEQUENCE: 13
aaaacaccac gtcgtccctg gct                                     23

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct; TD-BL

<400> SEQUENCE: 14
ctcatcaaat gtcaggatga acagcgtc                                28

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct; r52UR

<400> SEQUENCE: 15
agtggtcaga tgcccatcaa acgg                                    24

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct; r52LR

<400> SEQUENCE: 16
cgtttgcttg tgggttgtca cgtag                                   25

<210> SEQ ID NO 17
<211> LENGTH: 24
<212> TYPE: DNA
<213> ORGANISM: Artificial Sequence
<220> FEATURE:
<223> OTHER INFORMATION: Synthetic Construct; H19UR

<400> SEQUENCE: 17
agcttgcagc cttgcacagt ccag                                    24

<210> SEQ ID NO 18
<211> LENGTH: 24
<212> TYPE: DNA
<213> ORGANISM: Artificial Sequence
<220> FEATURE:
<223> OTHER INFORMATION: Synthetic Construct; H19LR
```

```
<400> SEQUENCE: 18
atggcccaca cagtgaccat cgga                                              24

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct; H74UR

<400> SEQUENCE: 19
gataaagtgg tcatcaagta cgcattcc                                          28

<210> SEQ ID NO 20
<211> LENGTH: 24
<212> TYPE: DNA
<213> ORGANISM: Artificial Sequence
<220> FEATURE:
<223> OTHER INFORMATION: Synthetic Construct; H74LR

<400> SEQUENCE: 20
gtactttccg atccgggtca tctc                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic Construct; H99UR

<400> SEQUENCE: 21
ctttgttttg atgagcggtc gctt                                              24

<210> SEQ ID NO 22
<211> LENGTH: 26
<212> TYPE: DNA
<213> ORGANISM: Artificial Sequence
<220> FEATURE:
<223> OTHER INFORMATION: Synthetic Construct; H99LR

<400> SEQUENCE: 22
ggttcgtgga ggatatcatt gctaca                                            26

<210> SEQ ID NO 23
<211> LENGTH: 24
<212> TYPE: DNA
<213> ORGANISM: Artificial Sequence
<220> FEATURE:
<223> OTHER INFORMATION: Synthetic Construct; H158UR

<400> SEQUENCE: 23
agccagcacc cagagcatcg aaca                                              24

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct; H158LR

<400> SEQUENCE: 24
tcccttgaac agcagcagga ggca                                              24

<210> SEQ ID NO 25
```

```
<211> LENGTH: 23
<212> TYPE: DNA
<213> ORGANISM: Artificial Sequence
<220> FEATURE:
<223> OTHER INFORMATION: Synthetic Construct; Alp-U

<400> SEQUENCE: 25
ttgagcgcaa ctacaagatc aac                                              23

<210> SEQ ID NO 26
<211> LENGTH: 23
<212> TYPE: DNA
<213> ORGANISM: Artificial Sequence
<220> FEATURE:
<223> OTHER INFORMATION: Synthetic Construct; Alp-L

<400> SEQUENCE: 26
ggtagtcagg ccatcgaggt agt                                              23

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct; Amy-U

<400> SEQUENCE: 27
ccacgcacat ccaactgaag                                                  20

<210> SEQ ID NO 28
<211> LENGTH: 23
<212> TYPE: DNA
<213> ORGANISM: Artificial Sequence
<220> FEATURE:
<223> OTHER INFORMATION: Synthetic Construct; Amy-L

<400> SEQUENCE: 28
gtcgaccacg ttgtattcct ttc                                              23

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct; prtT-U

<400> SEQUENCE: 29
aattcaggac ctccaatctg agt                                              23

<210> SEQ ID NO 30
<211> LENGTH: 23
<212> TYPE: DNA
<213> ORGANISM: Artificial Sequence
<220> FEATURE:
<223> OTHER INFORMATION: Synthetic Construct; prtT-L

<400> SEQUENCE: 30
gatggacatg acgagtgacc ata                                              23

<210> SEQ ID NO 31
<211> LENGTH: 23
<212> TYPE: DNA
<213> ORGANISM: Artificial Sequence
<220> FEATURE:
<223> OTHER INFORMATION: Synthetic Construct; 1258D-U

<400> SEQUENCE: 31
```

```
cagctttatc actttgggag ctg                                              23

<210> SEQ ID NO 32
<211> LENGTH: 24
<212> TYPE: DNA
<213> ORGANISM: Artificial Sequence
<220> FEATURE:
<223> OTHER INFORMATION: Synthetic Construct; 1258D-L

<400> SEQUENCE: 32
tgagtttggc agactatagg caag                                             24

<210> SEQ ID NO 33
<211> LENGTH: 27
<212> TYPE: DNA
<213> ORGANISM: Artificial Sequence
<220> FEATURE:
<223> OTHER INFORMATION: Synthetic Construct; B1035-CU

<400> SEQUENCE: 33
agcaacccaa gtgcgaagcc tatcgag                                          27

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct; B1035-CL

<400> SEQUENCE: 34
gaatccagtt gagtcggagc accgca                                           26

<210> SEQ ID NO 35
<211> LENGTH: 41
<212> TYPE: DNA
<213> ORGANISM: Artificial Sequence
<220> FEATURE:
<223> OTHER INFORMATION: Synthetic Construct; B1035-iU

<400> SEQUENCE: 35
ggcagcggtt acaggtaagc tcccaatgca aacaagacaa a                          41

<210> SEQ ID NO 36
<211> LENGTH: 42
<212> TYPE: DNA
<213> ORGANISM: Artificial Sequence
<220> FEATURE:
<223> OTHER INFORMATION: Synthetic Construct; B1035-iL

<400> SEQUENCE: 36
acatcacagg gtaggtccaa taaacatggc cacttttcag tt                         42

<210> SEQ ID NO 37
<211> LENGTH: 26
<212> TYPE: DNA
<213> ORGANISM: Artificial Sequence
<220> FEATURE:
<223> OTHER INFORMATION: Synthetic Construct; B1213-CU

<400> SEQUENCE: 37
ccgaaatcca aaagtagcct gtagtc                                           26

<210> SEQ ID NO 38
<211> LENGTH: 26
<212> TYPE: DNA
```

```
<213> ORGANISM: Artificial Sequence
<220> FEATURE:
<223> OTHER INFORMATION: Synthetic Construct; B1213-CL

<400> SEQUENCE: 38
cacctgagta gggctgtatt tgaaac                                        26

<210> SEQ ID NO 39
<211> LENGTH: 40
<212> TYPE: DNA
<213> ORGANISM: Artificial Sequence
<220> FEATURE:
<223> OTHER INFORMATION: Synthetic Construct; B1213-iU

<400> SEQUENCE: 39
ggcagcggtt acaggtagac ttgcagaaga tacccaactg                         40

<210> SEQ ID NO 40
<211> LENGTH: 38
<212> TYPE: DNA
<213> ORGANISM: Artificial Sequence
<220> FEATURE:
<223> OTHER INFORMATION: Synthetic Construct; B1213-iL

<400> SEQUENCE: 40
acatcacagg gtagggtttg ttccaacggc ataaggac                           38
```